United States Patent
Liu et al.

(10) Patent No.: US 11,628,440 B2
(45) Date of Patent: Apr. 18, 2023

(54) BIOLOGICAL SAMPLE REACTION BOX

(71) Applicant: LEADWAY (HK) LIMITED, Hong Kong (CN)

(72) Inventors: Shengqiang Liu, Zhejiang (CN); Tingfeng Gong, Zhejiang (CN); Huanjun He, Zhejiang (CN)

(73) Assignee: LEADWAY (HK) LIMITED, Hong Kong (CN)

( * ) Notice: Subject to any disclaimer, the term of this patent is extended or adjusted under 35 U.S.C. 154(b) by 0 days.

(21) Appl. No.: 15/741,664

(22) PCT Filed: Jun. 28, 2016

(86) PCT No.: PCT/CN2016/087518
§ 371 (c)(1),
(2) Date: Jan. 3, 2018

(87) PCT Pub. No.: WO2017/005123
PCT Pub. Date: Jan. 12, 2017

(65) Prior Publication Data
US 2018/0193842 A1  Jul. 12, 2018

(30) Foreign Application Priority Data

Jul. 3, 2015  (CN) .......................... 201510397989.9

(51) Int. Cl.
*B01L 3/00*   (2006.01)
*G01N 33/543*   (2006.01)
(Continued)

(52) U.S. Cl.
CPC .............. *B01L 3/523* (2013.01); *G01N 33/53* (2013.01); *G01N 33/543* (2013.01); *G01N 33/72* (2013.01);
(Continued)

(58) Field of Classification Search
CPC .......... B01L 3/523; B01L 3/5027; B01L 3/00; B01L 2200/141; B01L 2200/0689;
(Continued)

(56) References Cited

U.S. PATENT DOCUMENTS 4,883,763 A * 11/1989 Holen ................. B01L 3/50273
436/45
5,162,237 A   11/1992 Messenger et al.
(Continued)

FOREIGN PATENT DOCUMENTS

CN   101408549 A   4/2009
CN   102200536 A   9/2011
(Continued)

OTHER PUBLICATIONS

Davis, Lawrence. "Body Physics: Motion to Metabolism", 2010. Chapter 72, "Everyday Example: Driving", https://openoregon.pressbooks.pub/bodyphysics/chapter/newtons-3rd-law/ (Year: 2010).*
(Continued)

*Primary Examiner* — Benjamin R Whatley
*Assistant Examiner* — Curtis A Thompson
(74) *Attorney, Agent, or Firm* — Acuity Law Group, PC; Michael A. Whittaker

(57) ABSTRACT

A biological sample reaction vessel comprising a reagent storage portion and a push rod movable relative to the reagent storage portion is provided. The reagent storage portion comprises at least one reagent containing cavity, and the reagent containing cavity is sealed by a sealing element; and the push rod is connected to the sealing element, and the push rod is used for cooperation with an external device to separate the sealing element from the reagent storage portion. In reaction, the biological sample reaction vessel cooperates with a test cassette. By inserting the biological
(Continued)

sample reaction vessel into the external device, the reagent in the reagent storage portion can be released rapidly.

8 Claims, 11 Drawing Sheets

(51) Int. Cl.
| | |
|---|---|
| *G01N 33/72* | (2006.01) |
| *G01N 33/53* | (2006.01) |
| *G01N 21/03* | (2006.01) |
| *G01N 1/14* | (2006.01) |
| *G01N 1/24* | (2006.01) |
| *G01N 1/00* | (2006.01) |
| *G01N 1/02* | (2006.01) |
| *G01N 33/52* | (2006.01) |
| *G01N 21/05* | (2006.01) |
| *G01N 33/00* | (2006.01) |
| *G01N 21/51* | (2006.01) |
| *G01N 21/77* | (2006.01) |
| *G01N 33/487* | (2006.01) |
| *G01N 35/00* | (2006.01) |
| *B01J 37/36* | (2006.01) |

(52) U.S. Cl.
CPC ........... *B01D 2313/44* (2013.01); *B01J 37/36* (2013.01); *B01J 2220/62* (2013.01); *B01L 2200/0689* (2013.01); *B01L 2200/141* (2013.01); *B01L 2200/16* (2013.01); *B01L 2300/041* (2013.01); *B01L 2300/044* (2013.01); *B01L 2300/047* (2013.01); *B01L 2300/0609* (2013.01); *B01L 2300/0672* (2013.01); *B01L 2300/089* (2013.01); *B01L 2300/0854* (2013.01); *B01L 2300/0858* (2013.01); *B01L 2300/0861* (2013.01); *B01L 2300/0887* (2013.01); *B01L 2300/123* (2013.01); *B01L 2300/1877* (2013.01); *B01L 2300/1883* (2013.01); *B01L 2400/04* (2013.01); *B01L 2400/0457* (2013.01); *B01L 2400/0481* (2013.01); *B01L 2400/0633* (2013.01); *B01L 2400/0683* (2013.01); *B01L 2400/086* (2013.01); *G01N 21/0332* (2013.01); *G01N 21/51* (2013.01); *G01N 33/4875* (2013.01); *G01N 33/525* (2013.01); *G01N 33/528* (2013.01); *G01N 35/00069* (2013.01); *G01N 2001/002* (2013.01); *G01N 2001/027* (2013.01); *G01N 2001/1436* (2013.01); *G01N 2001/242* (2013.01); *G01N 2021/0325* (2013.01); *G01N 2021/0328* (2013.01); *G01N 2021/0375* (2013.01); *G01N 2021/0382* (2013.01); *G01N 2021/0385* (2013.01); *G01N 2021/052* (2013.01); *G01N 2021/054* (2013.01); *G01N 2021/056* (2013.01); *G01N 2021/7733* (2013.01); *G01N 2033/009* (2013.01); *G01N 2033/0081* (2013.01); *G01N 2035/00019* (2013.01)

(58) Field of Classification Search
CPC ........... B01L 2200/16; B01L 2200/025; B01L 2200/04; B01L 2200/10; B01L 2300/0887; B01L 2300/123; B01L 2300/089; B01L 2300/1883; B01L 2300/1877; B01L 2300/0861; B01L 2300/0854; B01L 2300/041; B01L 2300/0672; B01L 2300/044; B01L 2300/0816; B01L 2300/0867; B01L 2300/0645; B01L 2300/021; B01L 2300/06; B01L 2300/12; B01L 2300/0609; B01L 2300/0858; B01L 2300/047; B01L 2400/04; B01L 2400/0457; B01L 2400/086; B01L 2400/0683; B01L 2400/0481; B01L 2400/0633; B01L 3/502; G01N 35/00069; G01N 2035/00019; G01N 2001/1436; G01N 21/51; G01N 2033/0081; G01N 21/0332; G01N 2001/027; G01N 2001/002; G01N 2001/242; G01N 21/07; G01N 21/01; G01N 15/06; G01N 33/72; G01N 33/543; G01N 33/53; G01N 2033/009; G01N 33/4875; G01N 33/525; G01N 33/528; G01N 33/50; G01N 33/00; G01N 33/726; G01N 33/54366; G01N 33/723; G01N 33/48; G01N 2021/0375; G01N 2021/054; G01N 2021/7733; G01N 2021/056; G01N 2021/052; G01N 2021/0328; G01N 2021/0385; G01N 2021/0382; G01N 2021/0325; C12Q 1/28; C12M 3/00

See application file for complete search history.

(56) References Cited

U.S. PATENT DOCUMENTS

| | | | |
|---|---|---|---|
| 5,272,093 A | 12/1993 | Silva et al. | |
| 5,372,948 A | 12/1994 | Yip | |
| 5,385,847 A | 1/1995 | Yip et al. | |
| 6,656,428 B1 * | 12/2003 | Clark | B01L 3/502 |
| | | | 422/404 |
| 8,367,023 B2 | 2/2013 | Bae et al. | |
| 8,617,490 B2 | 12/2013 | Teng et al. | |
| 8,846,380 B2 | 9/2014 | Bae et al. | |
| 2002/0123059 A1 | 9/2002 | Ho | |
| 2004/0141880 A1 * | 7/2004 | Handler | G01N 35/00029 |
| | | | 506/15 |
| 2004/0189311 A1 * | 9/2004 | Glezer | B01L 3/5027 |
| | | | 324/444 |
| 2005/0221281 A1 | 10/2005 | Ho | |
| 2009/0093012 A1 * | 4/2009 | Bae | B01L 3/502 |
| | | | 435/29 |
| 2012/0027648 A1 | 2/2012 | Samper et al. | |
| 2013/0121898 A1 * | 5/2013 | Chen | B01L 3/5023 |
| | | | 422/554 |
| 2014/0127828 A1 | 5/2014 | Hou et al. | |
| 2015/0044764 A1 * | 2/2015 | Cha | B01L 3/502715 |
| | | | 435/288.7 |
| 2015/0147804 A1 * | 5/2015 | Cha | B01L 3/502 |
| | | | 435/288.7 |
| 2018/0141042 A1 * | 5/2018 | Taylor | G01N 35/00732 |
| 2020/0147607 A1 * | 5/2020 | Chen | B01L 3/50273 |

FOREIGN PATENT DOCUMENTS

| | | |
|---|---|---|
| CN | 102620959 A | 8/2012 |
| CN | 202903544 U | 4/2013 |
| CN | 104471392 A | 3/2015 |
| CN | 105013546 A | 11/2015 |
| CN | 105021544 A | 11/2015 |
| CN | 105021807 A | 11/2015 |
| CN | 204816573 U | 12/2015 |
| CN | 204832049 U | 12/2015 |
| CN | 204832194 U | 12/2015 |
| CN | 204832204 U | 12/2015 |
| CN | 204855358 U | 12/2015 |
| CN | 204855520 U | 12/2015 |
| CN | 205049571 U | 2/2016 |
| EP | 0469419 A2 | 2/1992 |
| EP | 0703453 A1 | 3/1996 |
| EP | 2591858 A2 | 5/2013 |
| JP | H07-5178 A | 1/1995 |

(56) References Cited

FOREIGN PATENT DOCUMENTS

| JP | 2009092643 | A  | 4/2009  |
|----|------------|----|---------|
| WO | 2009048217 | A1 | 4/2009  |
| WO | 2011116706 | A1 | 9/2011  |
| WO | 2012117244 | A2 | 9/2012  |
| WO | 2013162175 | A1 | 10/2013 |
| WO | 2014021539 | A1 | 2/2014  |
| WO | 2014159834 | A1 | 10/2014 |

OTHER PUBLICATIONS

Extended European Search Report issued in EP 16820774 dated Nov. 7, 2018 (9 pages total).
First Office Action issued by SIPO in Chinese Patent Application 201510397095.X dated Apr. 27, 2017 (8 pages total)—incl Engl lang transl.
First Office Action issued by SIPO in Chinese Patent Application 201510397932.9 dated May 18, 2016 (11 pages total)—incl Engl lang transl.
First Office Action issued by SIPO in Chinese Patent Application 201510397989.9 dated May 23, 2016 (14 pages total)—incl Engl lang transl.
First Office Action issued by SIPO in Chinese Patent Application 201510395786.6 dated Apr. 25, 2016 (9 pages total)—incl Engl lang transl.
Second Office Action issued by SIPO in Chinese Patent Application 201510397932.9 dated Feb. 14, 2017 (11 pages total)—incl Engl lang transl.
Second Office Action issued by SIPO in Chinese Patent Application 201510397989.9 dated Nov. 8, 2016 (14 pages total)—incl Engl lang transl.
Second Office Action issued by SIPO in Chinese Patent Application 201610543978.1 dated Dec. 7, 2017 (8 pages total)—incl Engl lang transl.
Third Office Action issued by SIPO in Chinese Patent Application 201510397989.9 dated May 17, 2017 (16 pages total)—incl Engl lang transl.
Response to the first Office Action issued by SIPO in Chinese Patent Application 201510397932.9 dated May 16, 2016 (7 pages total)—incl Engl lang transl.
Response to the first Office Action issued by SIPO in Chinese Patent Application 201510397989.9 dated Sep. 29, 2016 (14 pages total)—incl Engl lang transl.
Response to the first Office Action issued by SIPO in Chinese Patent Application 201510395786.6 dated May 6, 2016 (6 pages total)—incl Engl lang transl.
Response to the first Office Action issued by SIPO in Chinese Patent Application 201510397095.X dated Sep. 5, 2017 (6 pages total)—incl Engl lang transl.
Response to the First Office Action issued by SIPO in Chinese Patent Application 201610543978.1 dated Sep. 26, 2017 (9 pages total)—incl Engl lang transl.
Response to the second Office Action issued by SIPO in Chinese Patent Application 201510397932.9 dated Apr. 28, 2017 (9 pages total)—incl Engl lang transl.
Response to the second Office Action issued by SIPO in Chinese Patent Application 201510397989.9 dated Jan. 22, 2017 (10 pages total)—incl Engl lang transl.
Response to the second Office Action issued by SIPO in Chinese Patent Application 201610543978.1 dated Feb. 5, 2018 (7 pages total)—incl Engl lang transl.
Response to the third Office Action issued by SIPO in Chinese Patent Application 201510397989.9 dated Jul. 31, 2017 (10 pages total)—incl Engl lang transl.
International Search Report and Written Opinion issued in PCT/CN2016/087503 dated Oct. 9, 2016—Engl Transl only.
International Search Report and Written Opinion issued in PCT/CN2016/087518 dated Sep. 14, 2016—Engl Transl only.
International Search Report and Written Opinion issued in PCT/CN2016/087523 dated Sep. 22, 2016—Engl Transl only.
Office Action issued by SIPO in Chinese Patent Application No. 2015103979899 dated May 23, 2016 (7 pages total).
International Search Report and Written Opinion issued in PCT/CN2016/087518 dated Sep. 14, 2016—includes Engl lang transl (15 pages total).
Non Final Office Action issued by the USPTO in U.S. Appl. No. 15/741,688 dated Oct. 11, 2019.

* cited by examiner

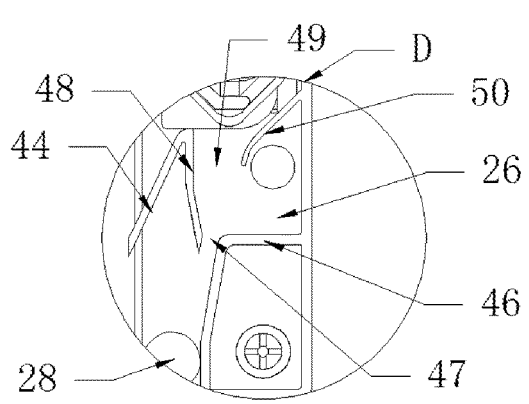
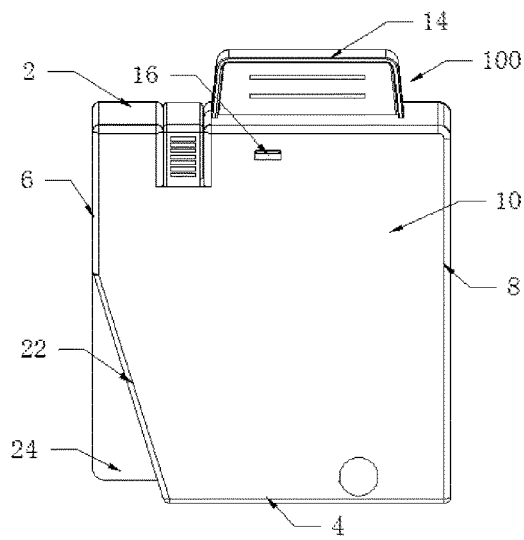
Fig.18    Fig.19
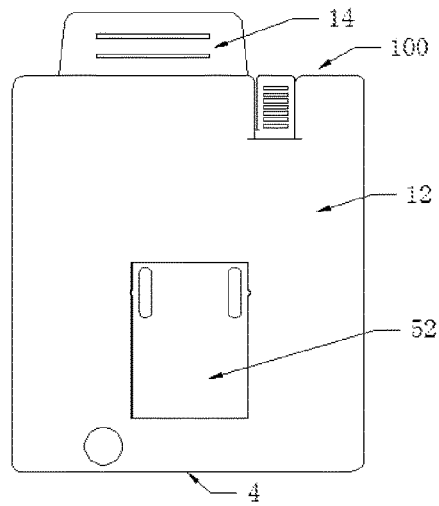
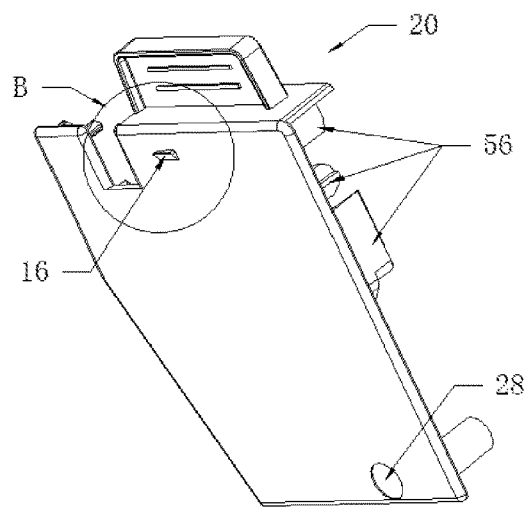
Fig.19A    Fig.20
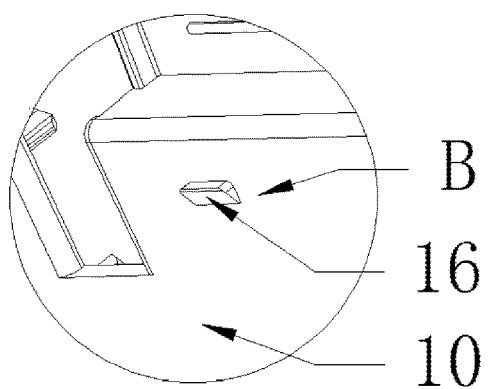
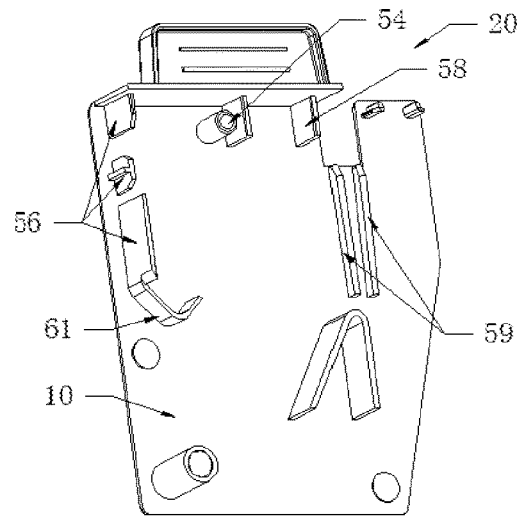
Fig.20A    Fig.20B

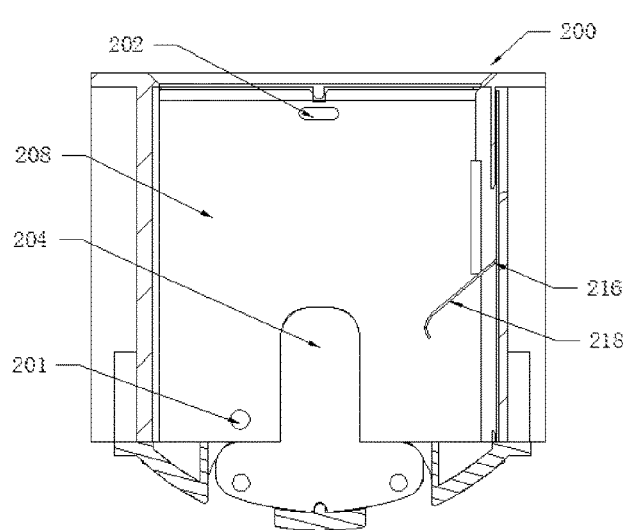
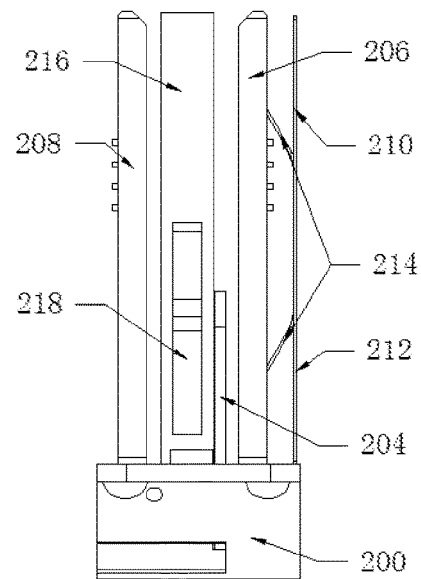
Fig.23   Fig.24
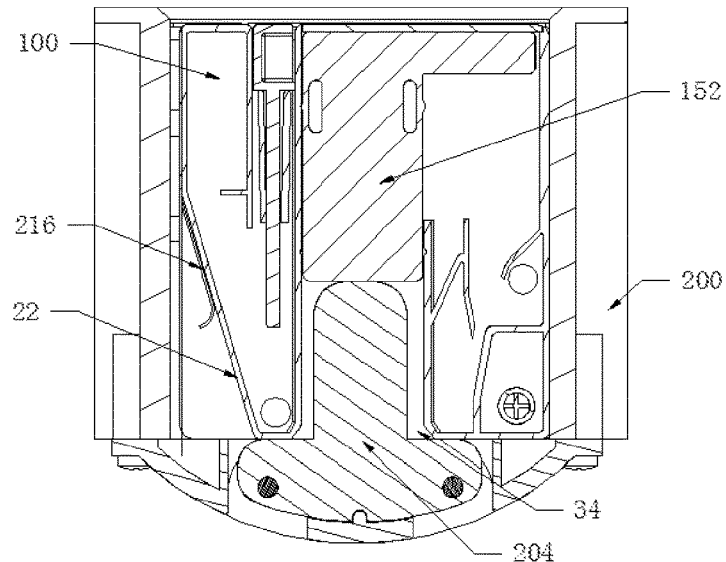
Fig.25
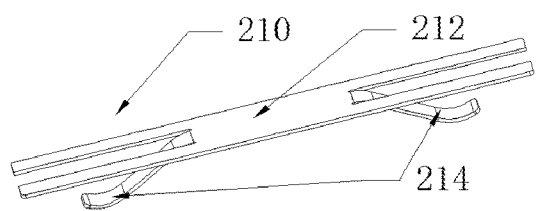 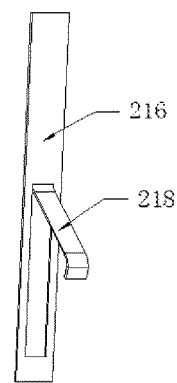
Fig.26   Fig.27

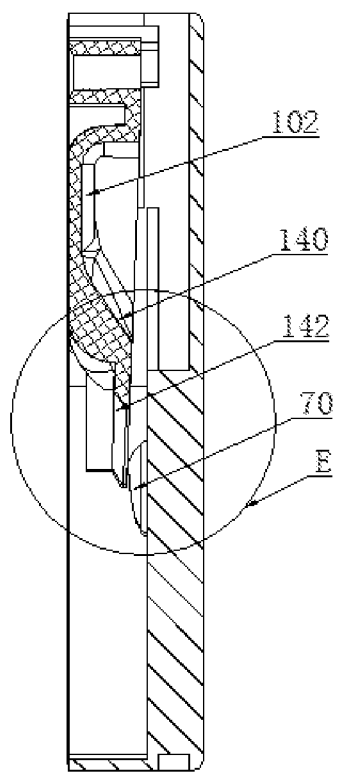
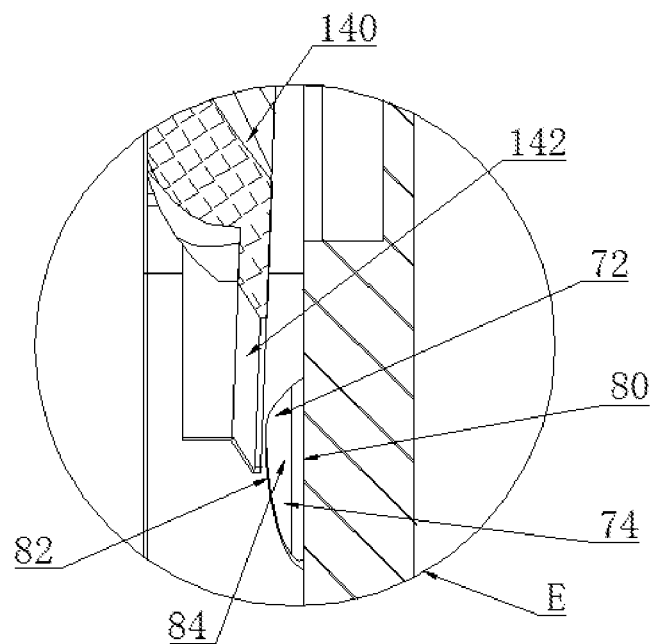
Fig.30A     Fig.30B
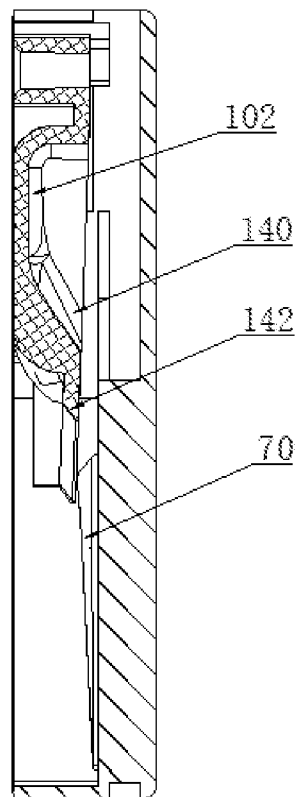
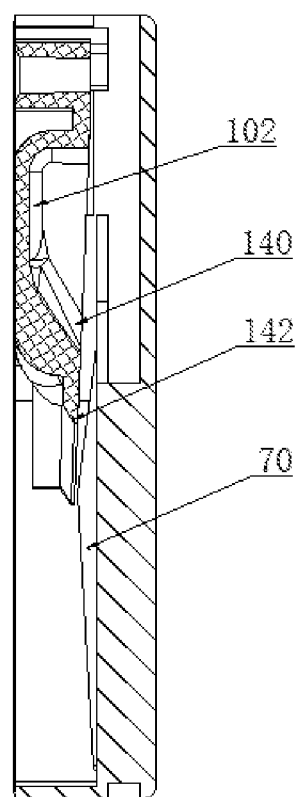
Fig.31     Fig.32

BIOLOGICAL SAMPLE REACTION BOX

CROSS-REFERENCE TO RELATED MATTERS

The present invention is filed under 35 U.S.C. § 371 as the U.S. national phase of International Patent Application No. PCT/CN2016/087518, filed Jun. 28, 2016, which designated the United States and claims priority to Chinese Patent Application No. 201510397989.9, filed Jul. 3, 2015, each of which is hereby incorporated in its entirety including all tables, figures and claims.

FIELD OF THE INVENTION

The present invention relates to the field of biological sample testing technology, and in particular, to a biological sample reaction vessel.

BACKGROUND OF THE INVENTION

Medical in vitro diagnosis plays a quite important role in today's medical industry, by means of which changes of various biological indicators in body fluid can be qualitatively or quantitatively measured so as to provide advice on disease diagnosis or treatment indicators and the like, for example, the test of glycosylated hemoglobin (HbA1c) in blood is essential for the diagnosis and control of diabetes.

The glycosylated hemoglobin is a binding product of hemoglobin and blood glucose in erythrocytes in human blood, and when the glucose concentration in the blood is high, the content of HbA1c formed by the human body is also relatively high. The average lifetime of the erythrocytes in the human body is 120 days, and before death of the cells, the content of HbA1c in the blood remains relatively constant, therefore the glycosylated hemoglobin test can usually reflect the blood glucose control condition of a patient in the past 8 to 12 weeks, and is not affected by occasional elevation or reduction of the blood glucose.

A variety of designs are also available in the prior art for testing the concentrations of analytes, for example:

As shown in FIG. 1, U.S. Pat. No. 1,562,237 discloses a reaction vessel. The reaction vessel includes a reaction channel and a liquid reagent storage portion, wherein a drying reagent is deployed on the reaction channel; the liquid reagent storage portion is used for storing a buffer solution or other liquid reagent; the liquid reagent storage portion includes a storage body 30' which is sealed by a sealing element or a thin film 32'; and the thin film 32' has a distal end 33', from which the thin film can be directly torn to separate the thin film from the storage body so that the reagent in the storage body is released into the reaction channel.

To release the liquid reagent, it needs to separate the thin film 32' manually which is originally sealed on the storage body 30', and then remove the thin film. Although the thin film can be torn off in the above manner to release the liquid reagent, it is very difficult to tear off the thin film from the storage body 30' through a segment of extended distal end 33', and the thin film is likely to be broken or incompletely torn off in the case of manual tearing with an excessive or insufficient force, such that the liquid reagent cannot be completely released, and the liquid reagent is insufficient during the test, resulting in a deviation of a test result; and on the other hand, in a non-test period, the thin film 32' is exposed to the air, thereby being prone to the risk of tear-off or damage by human or other factors.

As shown in FIG. 2, U.S. 5,272,093 discloses a "reagent container and delivery method thereof". The reagent container includes a reagent storage cavity 12' and a sealing element 40' sealed on the reagent storage cavity, wherein the sealing element is configured to be a folded arrangement of two layers, one layer being used for sealing the reagent storage cavity, the other layer extending to the outside of the reagent storage cavity to form an extension segment 42', and the extension segment 42' being used for tearing off the film and releasing the reagent in the reagent storage cavity. To release the liquid reagent, it needs to manually separate the sealing element 40', which is originally sealed on the reagent storage cavity 12', and the thin film is likely to be broken or incompletely torn off in the case of an excessive or insufficient force, such that the liquid reagent cannot be completely released, and the liquid reagent is insufficient during the test, resulting in a deviation of a test result.

As shown in FIG. 3, U.S. Pat. No. 8,846,380 discloses a "reaction vessel for testing glycated hemoglobin concentration". The reaction vessel includes a first area used for containing a blood sample of a kit, a second area used for containing a washing solution, a test area and a reagent bag, wherein a reagent and the washing solution in the reagent bag are separately stored and are sealed by an aluminum foil 120'. When the reagent bag is inserted into the reaction vessel, the aluminum foil is torn off by the reaction vessel, the reagent and the washing solution in the reagent bag are temporarily stored in a first reaction area and a second reaction area of the reaction vessel respectively, and sequentially react with the blood sample through rotation of the reaction vessel, thereby solving the storage and distribution problems of the reagent.

During testing with the reaction vessel, firstly, a release portion 130' on the aluminum foil needs to be manually folded, so that the release portion 130' is aligned with a holder in a test cassette, and the aligned reagent bag is inserted into the test cassette, so that the test cassette can cut off the release portion to separate the aluminum foil from the reagent bag. This design is relatively complex, the operation steps are troublesome, and moreover, manual alignment is required for the insertion, and failure of insertion into place is liable to occur which entails repeated insertion. On the other hand, the reaction vessel and the reagent bag are of a separate design, and due to the open design of the reaction vessel, in the case of improper operation, a foreign matter is very likely to drop into the reaction vessel, which affects the accuracy of the test result. Furthermore, in the non-test period, the release portion 130' is exposed to the air, thereby being prone to the risk of tear-off or damage by human or other factor.

The reaction vessel in the prior art includes a sampling needle, a reagent storage device, a reaction portion, a test area and the like. In a test reaction of the reaction vessel, the reagent in the reagent storage device is released to the reaction portion to participate in the test reaction. During the process of releasing the reagent to the reaction portion, as the reaction vessel is relatively small and structurally compact, and the distance between the reagent storage device and the wallboard of the reaction vessel is relatively small, an adsorption force for the reagent liquid is likely to be generated between the wallboard and a reagent release opening of the reagent storage device, such that a part of the reagent is left in a gap between the reagent release opening and the wallboard. In addition, in order to enable the reagent to enter the reaction portion more smoothly, a flow directing tip is further designed at the position of the reagent release opening of the reagent storage device, so that the reagent is guided by the flow directing tip after being released from the reagent release opening and finally enters the reaction portion under the action of gravity. Although the flow directing tip can better achieve flow guide, the flow directing tip is prone to a liquid suspension phenomenon when the reagent is released, so that a part of the reaction reagent is left on the flow directing tip. Furthermore, as the distance between the flow directing tip and the wallboard is relatively small, there is also a part of the reagent absorbed between the flow directing tip and the wallboard. Due to the partial residue of the reaction reagent, the reaction is not sufficient enough, resulting in reduced accuracy of the test result.

SUMMARY OF THE INVENTION

The technical problem to be solved by the present invention is to provide a biological sample reaction vessel in view of the above problems in the prior art.

In order to solve the above problem, a first technical solution of the present invention is as follows:

A biological sample reaction vessel is provided, wherein a reagent storage portion and a push rod movable relative to the reagent storage portion are packaged in the reaction vessel; the reagent storage portion comprises at least one reagent containing cavity, which is sealed by a sealing element; and the push rod is connected to the sealing element, and the push rod is used for cooperation with an external device to separate the sealing element from the reagent storage portion.

Preferably, a force-bearing portion cooperating with the external device is arranged on the push rod.

Preferably, an opening is formed in the reaction vessel, the force-bearing portion is exposed in the opening, and the force-bearing portion cooperates with the external device through the opening.

Preferably, the force-bearing portion is the back of the push rod.

Preferably, the force-bearing portion is a bottom surface of the push rod.

Preferably, a chute is formed in the reaction vessel, and the chute is in slide fit connection with the push rod.

Preferably, an isolating plate is arranged on the chute, and the isolating plate isolates the chute from the inner space of the reaction vessel.

Preferably, at least one limiting projection is arranged on at least one side face of the push rod.

Preferably, at least one hollowed-out slot is arranged at a position of the push rod close to an edge, the limiting projection is arranged on an outer side wall of the slot, and the limiting projection and the slot are arranged in pairs.

Preferably, a limiting groove cooperating with the limiting projection is formed in the reaction vessel.

A second technical solution of the present invention is as follows:

A testing system includes a reagent reaction vessel and a test device, wherein a reagent storage portion and a push rod movable relative to the reagent storage portion are packaged in the reagent reaction vessel; the reagent storage portion comprises at least one reagent containing cavity, which is sealed by a sealing element; the push rod is connected to the sealing element, and the push rod is used for cooperation with the test device to separate the sealing element from the reagent storage portion; and the test device includes a test cassette, an ejection rod is arranged in the test cassette, and the ejection rod cooperates with the push rod to separate the sealing element from the reagent storage portion.

Preferably, the ejection rod is movable relative to the test cassette.

Preferably, the ejection rod is arranged on a bottom plate of the test cassette.

Preferably, the ejection rod is arranged on an inner side panel of the test cassette.

Preferably, an opening is formed in the reagent reaction vessel, and the ejection rod penetrates through the opening to cooperate with the push rod.

Preferably, a movable plate is arranged on an inner side face of the test cassette.

Preferably, the movable plate includes a substrate and an elastic element, and the substrate is connected with the test cassette through the elastic element.

Preferably, the substrate is a heating plate.

Preferably, an elastic sheet is arranged on one inner side face of the test cassette.

Preferably, a groove is formed in an inner side face of the test cassette opposite to the movable plate.

A third technical solution of the present invention is as follows:

A reagent storage device includes a reagent containing cavity used for storing a solid particle reagent or a powder particle reagent, and the reagent containing cavity is sealed by a sealing element.

Preferably, the solid particle reagent or the powder particle reagent is a freeze-dried solid particle reagent or a freeze-dried powder particle reagent.

Preferably, the solid particle reagent is a latex freeze-dried pellet.

Preferably, the reagent storage device further includes a reagent containing cavity used for storing a liquid reagent or a powder reagent.

Preferably, an injection hole is formed in the reagent containing cavity used for storing the liquid reagent or the powder reagent, the injection hole communicates the reagent containing cavity with the external space, and the injection hole is sealed by a sealing element.

Preferably, the reagent storage device includes at least two reagent containing cavities, and the at least two reagent containing cavities are distributed in an array.

Preferably, the reagent storage device includes two reagent containing cavities, and the two reagent containing cavities are arranged horizontally arranged on left and right sides or longitudinally arranged up and down.

Preferably, the reagent storage device includes four reagent containing cavities, the four reagent containing cavities are arranged in two rows and four columns, two reagent containing cavities are arranged in each row, and one reagent containing cavity is arranged in each column.

Preferably, a cavity used for containing a desiccant is arranged on the back of the reagent storage device.

A fourth technical solution of the present invention is as follows:

A reagent reaction vessel includes a reagent storage portion, a reagent release portion and a reaction portion, wherein the reagent storage portion, the reagent release portion and the reaction portion are all arranged in the reaction vessel; the reagent storage portion includes at least one reagent containing cavity, which is sealed by a sealing element; the reagent release portion includes a push rod movable relative to the reagent storage portion, the push rod is connected to the sealing element, and the push rod is used for cooperation with an external device to separate the sealing element from the reagent storage portion; and the reaction portion includes at least one reaction area, and the reaction area receives a reagent released by the reagent storage portion.

Preferably, the reagent storage portion includes a plurality of reagent containing cavities, and the plurality of reagent containing cavities are arranged in an array.

Preferably, the reagent storage portion includes at least two columns of reagent containing cavities, and each column includes at least one reagent containing cavity.

Preferably, at least one of the reagent containing cavities is used for storing a solid particle reagent or a powder particle reagent.

Preferably, the reaction portion includes a first reaction area and a second reaction area, and the first reaction area and the second reaction area respectively receive and temporarily store the reagents released by different reagent containing cavities.

Preferably, the first reaction area is used for temporarily storing the solid particle reagent, the first reaction area includes a supporting portion and a blocking portion, a gap is formed between the supporting portion and the blocking portion, the maximum width of the gap is smaller than the minimum width of the solid particle reagent, and the supporting portion is a step.

Preferably, the first reaction area further includes a second baffle, the second baffle is obliquely arranged, a second gap is formed between the second baffle and the blocking portion, and the minimum width of the second gap is greater than the maximum width of the solid particle reagent.

Preferably, the blocking portion and the second baffle are baffles with radians.

Preferably, the second reaction area is used for temporarily storing a liquid reagent, a flow guide element is arranged on the second reaction area, and the flow guide element includes a first flow directing plate and a second flow directing plate.

A fifth technical solution of the present invention is as follows:

In application of a reagent reaction vessel in biological sample testing, the reagent reaction vessel includes a reagent storage portion, a reagent release portion and a reaction portion, wherein the reagent storage portion, the reagent release portion and the reaction portion are all arranged in the reaction vessel; the reagent storage portion includes at least one reagent containing cavity, which is sealed by a sealing element; the reagent release portion includes a push rod movable relative to the reagent storage portion, the push rod is connected to the sealing element, and the push rod is used for cooperation with an external device to separate the sealing element from the reagent storage portion; and the reaction portion includes at least one reaction area, and the reaction area receives a reagent released by the reagent storage portion.

A sixth technical solution of the present invention is as follows:

A test cassette is provided, wherein a movable plate is arranged in the test cassette, the movable plate includes a substrate and an elastic element, and the substrate is fixedly connected to an inner wall of the test cassette through the elastic element.

Preferably, the substrate is a heating plate.

Preferably, a groove is formed in an inner side face of the test cassette opposite to the movable plate.

Preferably, two elastic elements are provided.

Preferably, an elastic sheet is arranged on one inner side face of the test cassette adjacent to the movable plate.

Preferably, an ejection rod is arranged in the test cassette.

Preferably, the ejection rod is movable relative to the test cassette.

Preferably, the ejection rod is arranged on a bottom plate of the test cassette.

Preferably, a chamfer is arranged on an upper end part of the ejection rod.

Preferably, the ejection rod is arranged on an inner side panel of the test cassette.

A seventh technical solution of the present invention is as follows:

A biological sample analysis vessel includes a reaction portion, which includes at least one reaction area, wherein the at least one reaction area is a first reaction area, the first reaction area is used for temporarily storing a solid particle reagent, the first reaction area includes a supporting portion and a blocking portion, a gap is formed between the supporting portion and the blocking portion, and the maximum width of the gap is smaller than the minimum width of the solid particle reagent.

Preferably, the supporting portion is a step.

Preferably, the blocking portion is a baffle, which is marked as a first baffle.

Preferably, the first baffle is a vertical baffle, and a gap is formed between the bottom of the first baffle and the supporting portion.

Preferably, the first reaction area further includes a second baffle, the second baffle is obliquely arranged, a second gap is formed between the second baffle and the first baffle, and the minimum width of the second gap is greater than the maximum width of the solid particle reagent.

Preferably, the first baffle and the second baffle are baffles with radians.

Preferably, a powder drying reagent is fixedly deployed in the reaction area.

Preferably, the reaction portion further includes a second reaction area, and the second reaction area is used for temporarily storing a liquid reagent.

Preferably, a flow guide element is arranged on the second reaction area, and the flow guide element includes a first flow directing plate and a second flow directing plate.

Preferably, the solid particle reagent is a latex freeze-dried pellet reagent.

An eighth technical solution of the present invention is as follows:

A reagent storage device includes at least one reagent containing cavity, wherein an injection hole is formed in the at least one reagent containing cavity, the injection hole communicates the reagent containing cavity with the external space, and the reagent containing cavity and the injection hole are both sealed by a sealing element.

Preferably, the reagent containing cavity is used for storing a powder reagent or a liquid reagent.

Preferably, the reagent storage device includes a plurality of reagent containing cavities, and the plurality of reagent containing cavities are arranged in an array.

Preferably, the reagent storage device includes two reagent containing cavities, and the two reagent containing cavities are horizontally arranged on left and right sides.

Preferably, the reagent storage device includes two reagent containing cavities, and the two reagent containing cavities are longitudinally arranged up and down.

Preferably, the reagent storage device includes four reagent containing cavities, the four reagent containing cavities are arranged in two rows and four columns, two reagent containing cavities are arranged in each row, and one reagent containing cavity is arranged in each column.

Preferably, a cavity used for containing a desiccant is arranged on the back of the reagent storage device.

A ninth technical solution of the present invention is as follows:

A test reaction vessel includes a reagent storage device installed in the reaction vessel, wherein a reagent release site is arranged on the reagent storage device, the reaction vessel includes a wallboard facing to the reagent release site, a flow guide rib is arranged on the wallboard, the flow guide rib is in contact with liquid drops on a tail end of the reagent release site, and the flow guide rib is used for guiding the flow of the liquid drops on the tail end of the reagent release site.

Preferably, the flow guide rib is in contact with the tail end of the reagent release site.

Preferably, the reaction vessel further includes a reaction portion, and the flow guide rib projects into the reaction portion.

Preferably, the reaction vessel includes a side plate, and the flow guide rib forms a certain angle with respect to the side plate.

Preferably, the flow guide rib is arched.

Preferably, the flow guide rib includes a flow guide surface facing to the reagent release site, and the flow guide surface is a smooth curved surface.

Preferably, the flow guide rib further includes two side flow guide surfaces adjacent to the flow guide surface, and junctions of the two side flow guide surfaces and the wallboard are smooth curved surfaces.

Preferably, the reagent release site includes a reagent release opening.

Preferably, the reagent release site further includes a flow guide plate connected below the reagent release opening.

The biological sample reaction vessel mentioned herein can also be called a reaction vessel, reagent reaction vessel, biological sample analysis vessel or test reaction vessel.

Compared with the prior art, the present invention has the following beneficial effects:

1. The biological sample reaction vessel of the present invention is a single entirety, the reagent storage portion and the push rod are both packaged in the biological sample reaction vessel, and in reaction, the biological sample reaction vessel only needs to cooperate with a test cassette. With one operation, that is, inserting the biological sample reaction vessel into the external device, the reagent in the reagent storage portion can be released rapidly. The above structure reduces the manual operation portion in the test reaction to the simplest degree, thereby improving the automation level of the reaction, and during the reaction, the manual operation step only includes collecting a sample by using a sampling bar, adding the sample to the biological sample reaction vessel, and inserting the biological sample reaction vessel into the external device.

2. The portions constituting the biological sample reaction vessel of the present invention are all contained in the biological sample reaction vessel, in particular, the reagent storage portion and the push rod are contained in the biological sample reaction vessel, therefore the reagent storage portion and the push rod cannot be touched manually, and the push rod can be caused to operate only by means of an external thrust part of the test cassette in the external device projecting into the biological sample reaction vessel. Therefore, the situation that the sealing element is torn off from the reagent storage portion by improper manual operation or other factor at non-reaction time, resulting in earlier leakage of the reagent, is eliminated.

3. The opening in the biological sample reaction vessel of the present invention and the components are in gap fit, thereby providing a pure reaction space in the biological sample reaction vessel, guaranteeing the purity of the reaction reagents, avoiding the possibility that external foreign matters enter the biological sample reaction vessel, and improving the accuracy of the reaction.

4. The reagent storage device of the present invention is an independent component and is packaged in the biological sample reaction vessel, and the reagent storage device includes the reagent containing cavity used for storing the solid particle reagent or the powder particle reagent. The solid particle reagent or the powder particle reagent is sealed in the reagent storage device, thereby avoiding random movement of the reagent in the biological sample reaction vessel, avoiding the problem that the drying reagent needs to be fixed in the prior art, and meanwhile prolonging the useful life and storage life of the reagent at normal temperature in a sealed state, so that this reagent is distinctive from other reagents, so the reagent storage device is particularly suitable for reagents that are difficult to store under the normal temperature.

5. The reagent storage portion of the present invention comprises the latex freeze-dried pellet, thereby realizing maximum protection of the reactivity of the latex antibody on the one hand, and greatly prolonging the useful life and storage life of the reagent at normal temperature on the other hand.

6. According to the biological sample reaction vessel of the present invention, by configuring the number and the arrangement of the reagent containing cavities in the reagent storage portion, in combination with the automatic function of the push rod, simultaneous release of a plurality of reagents can be realized, and the plurality of reagents can be successively or simultaneously added according to the reaction time and sequence and cooperate with the drying reagent so as to accomplish various sample testing.

7. The testing system of the present invention can quickly push the ejection rod to operate when the biological sample reaction vessel is inserted, meanwhile the biological sample reaction vessel is quickly and stably fixed in the test cassette, which guarantees that the test area is aligned with an optical aperture, namely reagent release, biological sample reaction vessel fixation, test area focusing and other functions are accomplished at the same time by one operation, thereby maximally simplifying the reaction steps.

8. The flow guide rib is arranged on the reaction vessel of the present invention, when the liquid reagent is released from the reagent storage device into the reaction vessel, the liquid drops are caused to leave the reagent release site along the flow guide direction of the flow guide rib through the contact between the flow guide rib and the liquid drops on the tail end of the reagent release site, thereby avoiding the local residue of the liquid drops of the reagent, ensuring the accuracy of controlling the volume of the reagent and ensuring more sufficient reaction.

BRIEF DESCRIPTION OF THE DRAWINGS

FIG. 18 is an enlarged structural diagram at D in FIG. 5.

FIG. 19 is an axonometric schematic diagram of an external structure of the biological sample reaction vessel.

FIG. 19A is a schematic diagram of a rearview structure of the biological sample reaction vessel.

FIG. 20 is a structural schematic diagram of the upper cover in the biological sample reaction vessel.

FIG. 20A is an enlarged structural diagram at B in FIG. 20.

FIG. 20B is a structural schematic diagram of the upper cover in the biological sample reaction vessel at another angle.

FIG. 23 is a schematic diagram of a sectional structure of a test cassette.

FIG. 24 is a structural schematic diagram of internal components in the test cassette.

FIG. 25 is a schematic diagram of a sectional structure when a push rod is jacked up by an ejection rod after the biological sample reaction vessel is inserted into the test cassette.

FIG. 26 is a structural schematic diagram of an elastic element in the test cassette.

FIG. 27 is a structural schematic diagram of an elastic sheet in the test cassette.

FIG. 30 is a schematic diagram of a flow guide structure the backboard on the reaction vessel is looked through.

FIG. 30A is a structural schematic diagram of section H-H of FIG. 30.

FIG. 30B is an enlarged structural diagram at E in FIG. 30A.

FIG. 31 is a structural schematic diagram of one embodiment of the flow guide rib in the reaction vessel.

FIG. 32 is a structural schematic diagram of another embodiment of the flow guide rib in the reaction vessel.

DETAILED DESCRIPTION OF THE EMBODIMENTS

The present invention will be further described in detail below in conjunction with the drawings and embodiments, but the protection scope of the present invention is not limited thereto.

Figure 1:
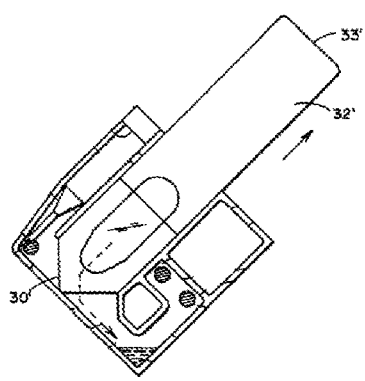
FIG. 1 is a structural schematic diagram of a reaction vessel in the prior art.
Figure 2:
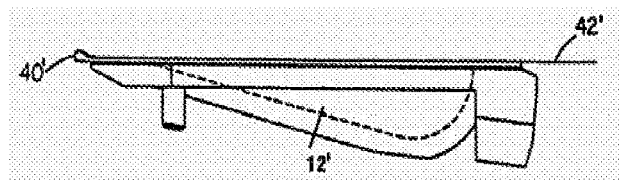
FIG. 2 is a structural schematic diagram of a reagent container in the prior art.
Figure 3:
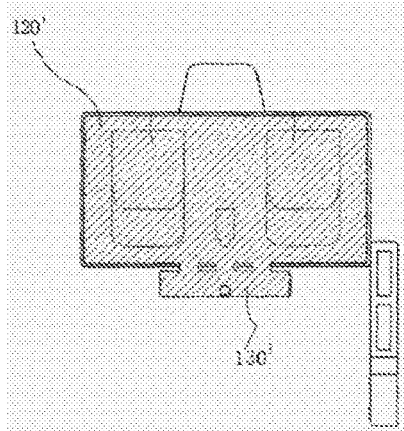
FIG. 3 is a schematic diagram of a partial structure of the reaction vessel in the prior art.
Figure 4:
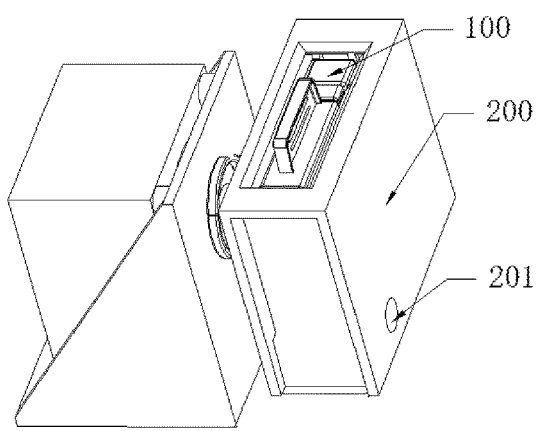
FIG. 4 is an isometric schematic diagram of a partial structure in a testing system.

As shown in FIG. 4, a testing system of the present invention is used for quickly testing the concentration of an analyte in a biological sample, and includes a biological sample reaction vessel 100 and an external device, the external device is a device other than a body of the biological sample reaction vessel 100, wherein the external device is also called a test device, a test cassette 200 is arranged on the external device or the test device, and the biological sample reaction vessel 100 and the test cassette 200 are cooperatively used. The biological sample reaction vessel 100 serves as a reaction container and can achieve storage of a plurality of reagents, sequential addition of a plurality of reagents, waste liquid recycle and other functions. The test cassette 200 is used for placing the biological sample reaction vessel 100, the test cassette 200 is installed on the test device, the test device provides mechanical power and control for rotation of the biological sample reaction vessel 100, uniform mixing of the reagents in the biological sample reaction vessel 100, reagent release and the like, moreover, an optical device is further arranged on the external device, and the optical device is used for testing the concentration of the analyte in a liquid sample.

Figure 5:
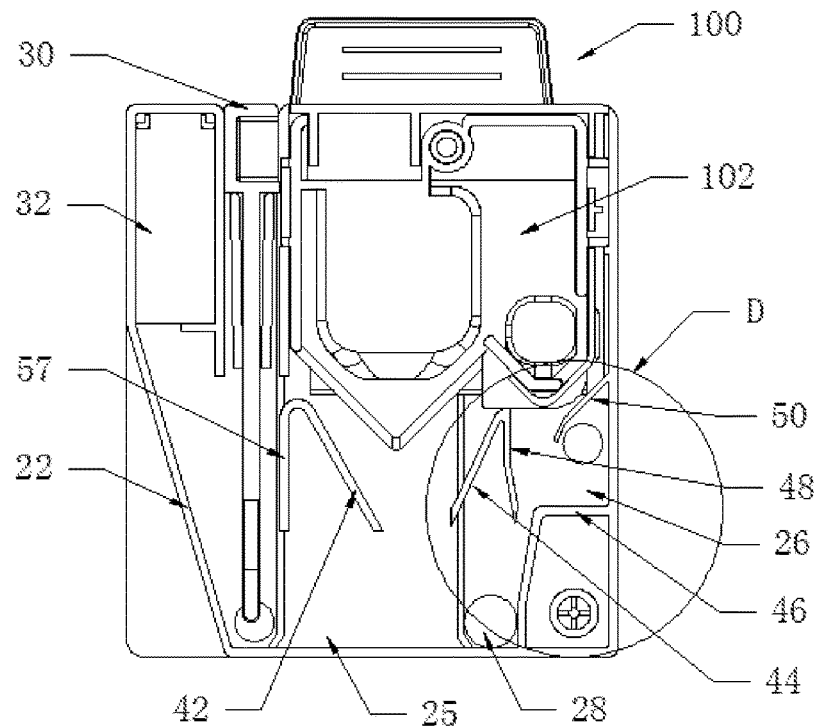
FIG. 5 is a structural schematic diagram after a panel in a biological sample reaction vessel is hidden.
Figure 6:
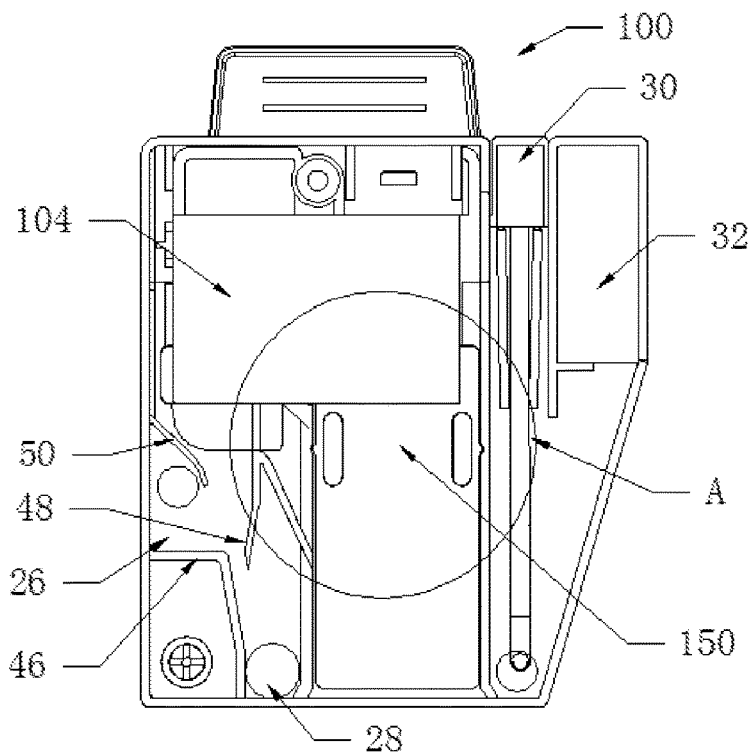
FIG. 6 is a structural schematic diagram after a backboard in the biological sample reaction vessel is hidden.

As shown in FIGS. 5 and 6, a reagent storage portion 102, a reagent release portion 150, a reaction portion and a test area 28 are arranged in the biological sample reaction vessel 100. The reagent storage portion 102 and the reagent release portion 150 are both packaged in the biological sample reaction vessel 100. Preferably, a cavity is formed in the biological sample reaction vessel 100, and the reagent storage portion 102 is contained in the cavity. The reagent storage portion 102 is an independent component and is packaged in the biological sample reaction vessel 100, which is beneficial for fast assembly of the biological sample reaction vessel. The reagent storage portion 102 is used for sealing and storing a solid particle, powder or liquid reagent, and the reagent release portion 150 can, through cooperation with the test cassette 200 in the test device, quickly open the reagent storage portion 102 to release the reagent into the reaction portion of the biological sample reaction vessel 100. The reaction portion is used for temporary storage, mixing and reaction of the biological sample and the reagent, and an intermediate product or a final product of the reaction is tested through the test area 28.

Figure 7:
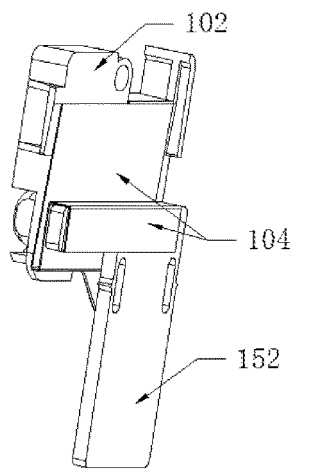
FIG. 7 is a schematic diagram of a connecting structure of a reagent storage portion, a sealing element and a reagent release portion.
Figure 8:
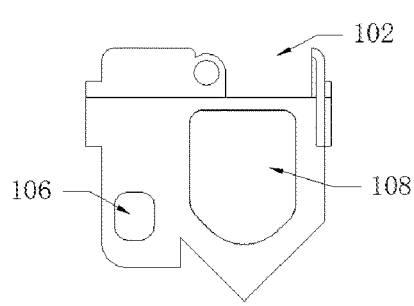
FIG. 8 is a structural schematic diagram of the reagent storage portion.

As shown in FIGS. 7 and 8, the reagent storage portion 102 includes at least one reagent containing cavity, and the reagent storage portion 102 is sealed by a sealing element 104, namely, the reagent containing cavity is sealed by the sealing element 104. The reagent storage portion 102 is also called a reagent storage device, the reagent storage portion 102 includes a plurality of reagent containing cavities, and the plurality of reagent containing cavities are arranged in an array. The number of the reagent containing cavities is set according to the categories of the reagents needed in the test reaction and the addition sequence, for example, one, two or more, the reagent containing cavities are independent from each other, namely the plurality of reagent containing cavities are provided with gaps therebetween and are distributed in the array. For example, two reagent containing cavities can be horizontally arranged in a row, can also be longitudinally arranged in a column and can also be diagonally; and as another example, the plurality of reagent containing cavities can also be distributed at intervals in a staggered manner. The capacity of the reagent containing cavities is also set according to the dosage needed in the test reaction.

Preferably, the reagent storage portion includes at least two columns of reagent containing cavities, and each column includes at least one reagent containing cavity.

Preferably, as shown in FIG. 8, the reagent storage portion 102 includes two reagent containing cavities, and the two reagent containing cavities are horizontally arranged on left and right sides. That is, a reagent containing cavity 106 and a reagent containing cavity 108 are distributed in one row and two columns on the left and right sides, and the bottoms of the reagent containing cavities are approximately located on the same horizontal line. Therefore, when the sealing element 104 is torn off, the reagents in the reagent containing cavity 106 and the reagent containing cavity 108 can be released into the biological sample reaction vessel 100 together.

Figure 9:
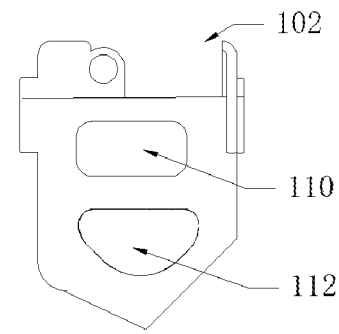
FIG. 9 is a structural schematic diagram of one embodiment of the reagent storage portion.

As shown in FIG. 9, in an embodiment of the reagent storage portion 102, the two reagent containing cavities are longitudinally arranged, namely, a reagent containing cavity 110 and a reagent containing cavity 112 are distributed in two rows and one column up and down, when the sealing element 104 is partially torn off, the reagent containing cavity 112 located in the lower row preferentially releases the reagent, and the sealing element 104 is further torn off according to the requirement of the reaction time, so that the reagent containing cavity 110 located in the upper row releases the reagent. The reagents can be added in sequence by controlling the tear-off degree of the sealing element 104 so as to control the implementation of the reaction.

Figure 10:
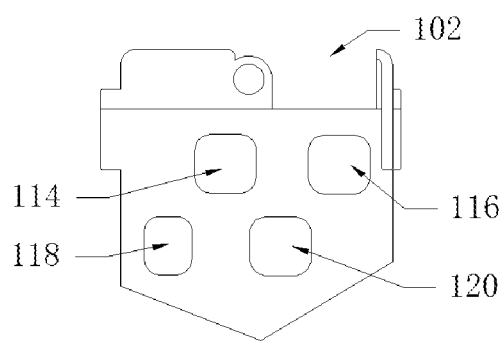
FIG. 10 is a structural schematic diagram of another embodiment of the reagent storage portion.

As shown in FIG. 10, in another embodiment of the reagent storage portion, four reagent containing cavities are arranged in an array, namely, a reagent containing cavity 114, a reagent containing cavity 116, a reagent containing cavity 118 and a reagent containing cavity 120 are arranged in two rows and four columns. With the torn-off degree of the sealing element 104 being controlled, the reagents in the reagent containing cavity 118 and the containing cavity 120 in the lower row are preferentially released, and then the reagents in the cavities in the upper row are released.

Preferably, the reagent storage device includes a reagent containing cavity used for storing a solid particle reagent or a powder particle reagent. The solid particle reagent or the powder particle reagent is sealed in the reagent storage device, thereby avoiding random movement of the reagent in the biological sample reaction vessel, avoiding the problem that a drying reagent needs to be fixed in the prior art, and meanwhile prolonging the useful life and storage life of the reagent at normal temperature in a sealed state, so that this reagent is distinctive from other reagents, so the reagent storage device is particularly suitable for reagents that are difficult to store under the normal temperature.

Preferably, the solid particle reagent or the powder particle reagent is a freeze-dried solid particle reagent or a freeze-dried powder particle reagent. Preferably, the solid particle reagent is a latex freeze-dried pellet. The latex freeze-dried pellet achieves maximum protection of the reactivity of the latex antibody on the one hand, and greatly prolong the useful life and storage life of the reagent under the normal temperature on the other hand.

Preferably, the reagent storage device further includes a reagent containing cavity used for storing a liquid reagent. The reagent containing cavity can be used for storing a solid particle, powder particle or liquid reagent, and it can be set according to test requirement.

Figure 8A:
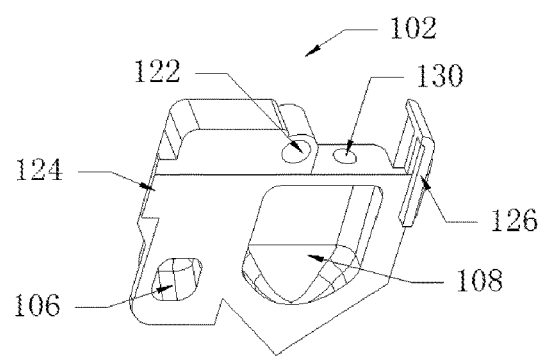
FIG. 8A is a structural schematic diagram of the reagent storage portion at one angle.

Preferably, as shown in FIG. 8A, an injection hole 130 is formed in at least one reagent containing cavity, the injection hole 130 communicates the reagent containing cavity with the external space, and the reagent containing cavity and the injection hole 130 are both sealed by the sealing element 104. Preferably, the injection hole 130 is formed in the reagent containing cavity used for storing a powder reagent or a liquid reagent. In order to seal the liquid reagent or the powder reagent more simply, in a sealing process, the reagent containing cavity is firstly sealed by the sealing element 104 and the injection hole 130 is exposed at the outside, then the liquid reagent or the powder reagent is injected to the reagent containing cavity, and thereafter the injection hole 130 is sealed so as to guarantee the sealing effect and reduce the difficulty of sealing the liquid reagent or the powder reagent. The reagent containing cavity and the injection hole can be sealed by the same sealing element in different steps and at different time, or can be separately sealed by two sealing elements, for example, the injection hole is sealed by a sealing stopper, and the like.

Figure 8B:
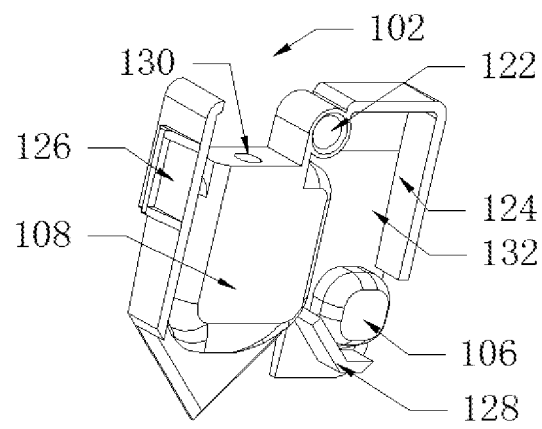
FIG. 8B is a structural schematic diagram of the reagent storage portion at another angle.

Preferably, as show in FIG. 8B, a cavity 132 used for mounting a desiccant is further arranged on the back of the reagent storage portion 102. When the reagent storage portion 102 is installed in the biological sample reaction vessel 100, the desiccant is installed in the cavity 132 by means of cooperation between the cavity 132 and the inner wall of a panel 10.

Preferably, the reagent storage portion 102 includes two reagent containing cavities, and the two reagent containing cavities are respectively used for storing a solid particle reagent and a liquid reagent. The embodiment is illustrated in detail by using an example that the reagent storage portion 102 includes two reagent containing cavities 106, 108, the reagent containing cavity 106 is used for storing the solid particle reagent, the reagent containing cavity 108 is used for storing the liquid reagent, and the injection hole 130 is formed in an upper end of the reagent containing cavity 108. In the sealing process, the solid particle reagent is placed in the reagent containing cavity 106 at first, cavity openings of the reagent containing cavity 106 and the reagent containing cavity 108 are sealed by the sealing element 104, then the liquid reagent is injected into the reagent containing cavity 108, and thereafter the injection hole 130 is sealed by the sealing element 104.

Preferably, the bottom of the reagent containing cavity is designed into the shape of an inclined plane. When the reagent is released, the reagent can flow out conveniently and quickly, thereby reducing the residual reagent in the containing cavity as much as possible and guaranteeing the accuracy of controlling the volume of the reagent.

Figure 7A:
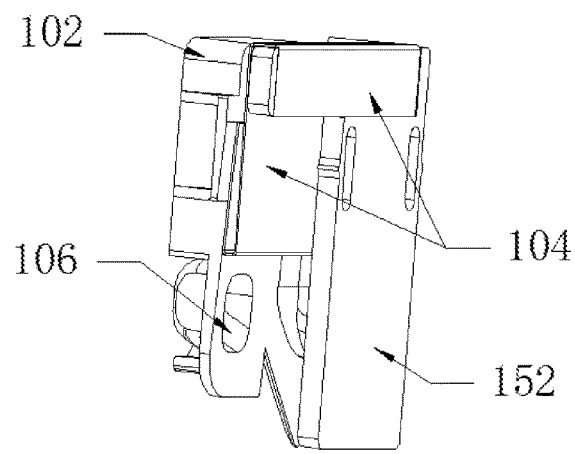
FIG. 7A is a structural schematic diagram after the sealing element is torn off in FIG. 7.

As shown in FIG. 7, the reagent storage portion 102 is sealed by the sealing element 104, namely the reagent is sealed in the reagent containing cavity, the sealing element 104 can be torn off from the reagent containing cavity under the action of an external force, the sealing element 104 can be torn off from left to right, from bottom to top or the like, description is made herein using an example that the sealing element is torn off from bottom to top, as shown in FIG. 7A. The sealing element 104 can be an aluminum foil, a thin film or other sealing element conventionally used in the prior art.

As shown in FIGS. 29, 30, 30A and 30B, the reaction vessel includes the reagent storage portion 102 installed in the reaction vessel, a reagent release site is arranged on the reagent storage portion 102, the reaction vessel 100 includes a wallboard facing to the reagent release site, a flow guide rib 70 is arranged on the wallboard, the flow guide rib 70 is in contact with liquid drops on a tail end of the reagent release site, and the flow guide rib 70 is used for guiding the flow of the liquid drops on the tail end of the reagent release site. The reagent release site refers to a position where the liquid reagent flows out from the reagent storage device and leaves the reagent storage device, namely, a liquid passage of the liquid reagent on the reagent storage device. Correspondingly, the tail end of the reagent release site refers to the tail end of the liquid passage. The wallboard is a backboard 12 or an isolating plate 36 on the reaction vessel 100 mentioned below, when the flow guide rib 70 is installed on the backboard 12, the reagent release portion adopts the manual mode in the prior art, and when the flow guide rib 70 is installed on the isolating plate 36, the reagent release portion adopts the automatic mode herein. When the liquid reagent is released from the reagent storage device into the reaction vessel, a part of liquid drops remain on the tail end of the reagent release site or is adsorbed between the tail end of the reagent release site and the wallboard, and the liquid drops are caused to leave the reagent release site along the flow directing direction of the flow guide rib through the contact between the flow guide rib and the liquid drops on the tail end of the reagent release site, thereby avoiding the local residue of the liquid drops of the reagent, ensuring the accuracy of controlling the volume of the reagent and ensuring more sufficient reaction.

Figure 33:
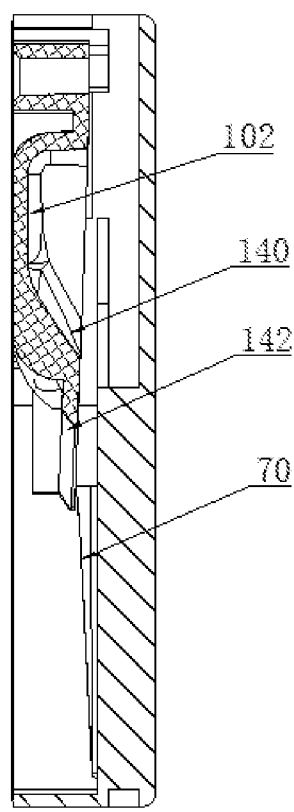
FIG. 33 is a structural schematic diagram of yet another embodiment of the flow guide rib in the reaction vessel.
Figure 34:
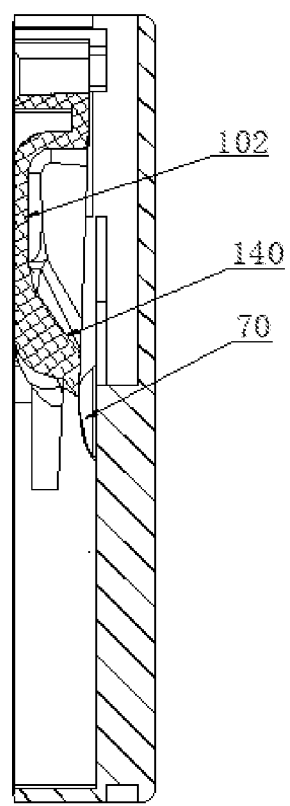
FIG. 34 is a structural schematic diagram of one embodiment of the flow guide rib and a reagent storage device in the reaction vessel.

In the embodiment shown in FIG. 34, the reagent release site includes a reagent release opening 140. The bottom of the reagent release opening 140 is the tail end of the reagent release site. In the embodiment shown in FIGS. 30 to 33, the reagent release site further includes a flow guide plate 142 connected below the reagent release opening 140. The flow guide plate 142 is used for guiding the flow of the liquid, so that the liquid regent leaves the reagent storage portion 102 more smoothly, the flow guide plate 142 is in the shape of a sharp corner, and the bottom of the flow guide plate 142 is the tail end of the reagent release site.

Preferably, the flow guide rib 70 is in contact with the tail end of the reagent release site. Therefore, the contact surface of the liquid drops on the tail end of the reagent release site and the flow guide rib 70 is increased, and accordingly the flow of the liquid drops is directed more quickly. As shown in FIG. 30B, the flow guide rib includes a contact end 72 and a guide end 74, which are connected successively, the contact end 72 is in contact with the liquid drops on the tail end of the reagent release site or in contact with the tail end of the reagent release site, and the guide end 74 extends downward from the contact end 72. Preferably, the flow guide rib is in the shape of a thin strip. The contact end 72 is used for contacting the liquid drops and directing the flow of the liquid drops onto the guide end 74, the guide end 74 is used for guiding the liquid drops on the contact end 72 to a specified position of the reaction vessel 100. The area of the cross section of the guide end 74 is successively reduced from top to bottom, and the bottom of the guide end is formed into a tip, which is conducive to directing the flow of the liquid drops so as to reduce the liquid suspension phenomenon on the bottom of the guide end as much as possible. Due to the contact of the contact end and the liquid drops, the flow of the liquid drops can be quickly directed. The closer the contact end to the tail end of the reagent release site, the larger the contact surface between the contact end and the liquid drops is, and the more obvious the flow directing function of the flow guide rib is.

As shown in FIGS. 31 to 33, the reaction vessel 100 further includes a reaction portion, and the flow guide rib 70 projects into the reaction portion. That is, the guide end 74 of the flow guide rib 70 projects into the reaction portion and comes into contact with the liquid reagent in the reaction portion. By means of the extension design of the flow guide rib 70, the liquid drops can be quickly and accurately guided into the reaction portion. Meanwhile, after the flow of the large liquid drops adsorbed to the tail end of the reagent release site are directed by the flow guide rib, tiny liquid points may be suspended on the bottom of the guide end of the flow guide rib, the liquid drops suspended on the guide end come into contact with the liquid reagent in the reaction portion and then are taken away, thereby avoiding the residual small liquid drops on the flow guide rib. In the embodiment shown in FIG. 32, the contact end 72 of the flow guide rib 70 extends upward, which is conducive to quickly guiding the liquid in the reagent storage device to enter the reaction portion.

In the embodiment shown in FIGS. 29 to 34, the reaction vessel 100 includes a side plate, and the flow guide rib 70 forms a certain angle with respect to the side plate. The flow guide rib 70 is obliquely arranged or arranged to be parallel to the side plate. The side plate is a left side plate 6 or a right side plate 8 on the reaction vessel 100 mentioned below. Preferably, the flow guide direction of the flow guide rib 70 is consistent with the flow direction of the liquid in the reagent storage device. When the flow direction of the liquid reagent released from the reagent storage device is vertical to the horizontal plane, the flow guide rib is arranged to be vertical to the horizontal plane; when the reagent storage device of the reaction vessel releases the reagent, the reaction vessel inclines at an angle relative to the horizontal plane, at this time, the flow direction of the liquid reagent forms an inclination angle with respect to the side plate for release, the flow guide rib is obliquely arranged, and the inclination direction of the flow guide rib is the flow direction of the liquid in the reagent storage device. The flow guide direction of the flow guide rib is consistent with the flow direction of the liquid in the reagent storage device, which is conducive to reducing the resistance in a flow directing process to enable the reagent to flow down quickly.

Preferably, the flow guide rib is arched. Preferably, the longitudinal section of the flow guide rib is a triangle. The triangle is a rounded triangle. The triangle is selected from a right triangle, an obtuse triangle or an acute triangle. In the embodiment shown in FIG. 33, the longitudinal section of the flow guide rib 70 is a right triangle, one right angle side of the right triangle is fixedly arranged on the wallboard, the portion on the flow guide rib 70 capable of contacting the liquid drops is the contact end 72, and the portion below the contact end 72 is the guide end 74. In the embodiment shown in FIGS. 30A, 31 and 32, the longitudinal section of the flow guide rib 70 is an obtuse triangle, the maximum hypotenuse of the obtuse triangle is fixedly arranged on the wallboard, the portion on the flow guide rib 70 capable of contacting the liquid drops is the contact end 72, the portion below the contact end 72 is the guide end 74, and the portion above the contact end 72 is an extension portion of the contact end 72.

As shown in FIG. 30B, the flow guide rib 70 includes an installation surface 80, a flow guide surface 82 opposite to the installation surface and two side flow guide surfaces 84 adjacent to the installation surface, and the installation surface 80 is fixedly arranged on the wallboard. The flow guide surface 82 faces to the reagent release site, the flow guide surface 82 is a smooth curved surface, and the junctions of the two side flow guide surfaces 84 and the wallboard are smooth curved surfaces. Due to the design of the smooth curved surfaces, the flow directing of the flow guide rib is smoother, and the resistance is smaller.

Figure 11:
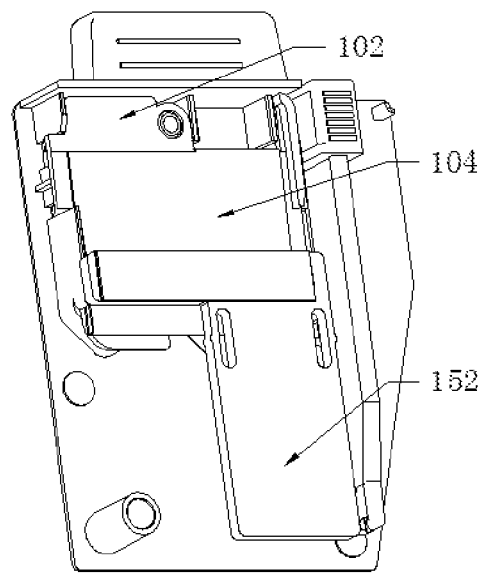
FIG. 11 is a schematic diagram of a connecting structure of an upper cover, the reagent storage portion and a reagent release portion in the biological sample reaction vessel.
Figure 12:
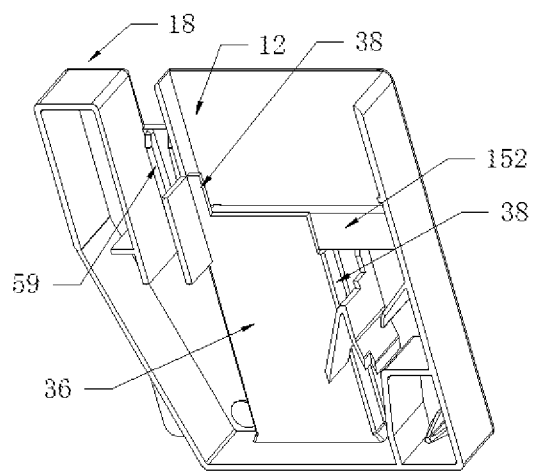
FIG. 12 is a schematic diagram of a connecting structure of a box body and a push rod in the biological sample reaction vessel.

As shown in FIGS. 11 and 12, the reagent release portion 150 includes a push rod 152, the push rod 152 is connected to the sealing element 104, and the push rod 152 is used for cooperation with an external device to separate the sealing element from the reagent storage portion. As shown in FIG. 7A, namely, the sealing element 104 is adhered or fixed to the push rod 152, when the external device acts on the push rod 152, the push rod 152 cooperates with the inner wall of the biological sample reaction vessel 100 to generate movement relative to the reagent storage portion 102, the push rod 152 drives, while moving, the sealing element 104 to move relative to the reagent storage portion 102, namely, an action of tearing off the sealing element 104, so that the reagent in the reagent containing cavity is released into the biological sample reaction vessel 100. The movement of the push rod 152 relative to the reagent storage portion 102 can be implemented in a manner of from left to right, from right to left, from bottom to top, etc.

Preferably, as shown in FIG. 7, one end of the sealing element 104 seals the reagent storage portion 102, and the other end of the sealing element is adhered to the push rod 152 after being folded.

Preferably, a force-bearing portion cooperating with the external device is arranged on the push rod 152. The force-bearing portion is used for bearing the thrust provided by the external device.

Preferably, the push rod 152 is entirely contained in the biological sample reaction vessel, and a thrust part of the external device needs to project into the biological sample reaction vessel 100 or act on the force-bearing portion of the push rod 152 in other manner. The push rod 152 is entirely contained in the biological sample reaction vessel 100, a human hand cannot touch the push rod in the biological sample reaction vessel, the push rod 152 cannot be caused to operate manually with bare hands, and the push rod 152 can only be caused to operate by using an external tool. Therefore, the possibility of earlier leakage of the reagent in a non-test period caused by manual tear-off or damage of the sealing element 104 due to misoperation or other reason is avoided.

Figure 13:
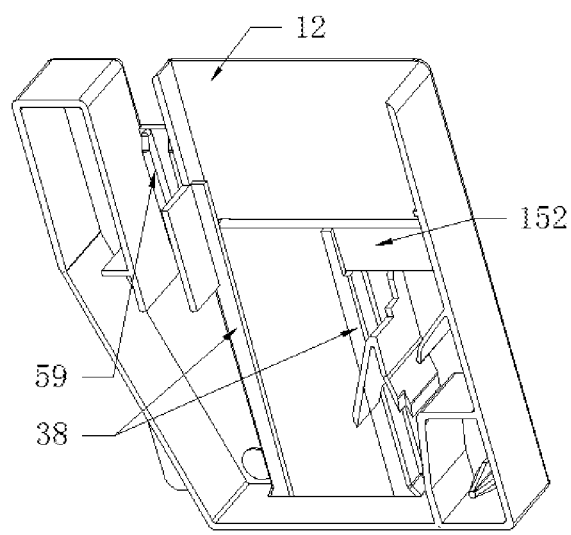
FIG. 13 is a structural schematic diagram of another embodiment of the connection of the box body and the push rod in the biological sample reaction vessel.

Preferably, as shown in FIG. 13, a chute 38 is formed in the biological sample reaction vessel 100. On the one hand, the chute 38 embeds the push rod 152 in a slide way, and on the other hand, the chute 38 is in slide fit with the push rod 152. In an embodiment, the chute 38 is formed the backboard 12, the chute 38 can be designed to only consist of the backboard 12 and two groove sides, and in this case, two side parts of the push rod 152 are partially contained in the chute 38.

Figure 12A:
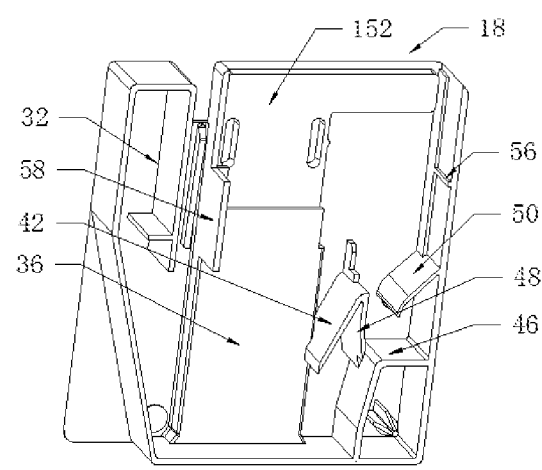
FIG. 12A is a structural schematic diagram after the push rod slides relative to the box body in the biological sample reaction vessel.

Preferably, as shown in FIGS. 12 and 12A, the isolating plate 36 is arranged on the chute 38, and the isolating plate 36 isolates the chute 38 from the inner space of the biological sample reaction vessel 100. In an embodiment, the chute 38 is a columnar body with at least one open end, four side faces of the columnar body are respectively formed by part of the backboard 12, two side edges of the chute 38 and the isolating plate 36, that is to say, the chute 38 is hermetically connected with the isolating plate 36, the isolating plate 36 isolates the chute 38 from the inner space of the biological sample reaction vessel 100, and the height of the isolating plate 36 is designed in such a way that the reaction liquid will not flow to the outside of the biological sample reaction vessel. The chute 38 is designed into an independent area, the push rod 152 or an external thrust part is isolated from the reagent, therefore it can be avoided that a part of reagent is taken away by the contact of the push rod 152 or the external thrust part and the reaction reagent.

Figure 14:
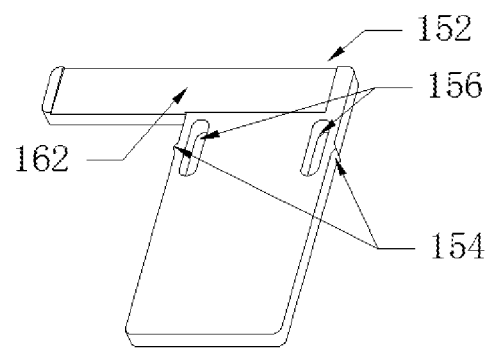
FIG. 14 is an axonometric structural diagram of a release portion in the biological sample reaction vessel.

Preferably, as shown in FIG. 14, at least one limiting projection 154 is arranged on at least one side face of the push rod 152. The limiting projection 154 allows the push rod 152 to be installed in the biological sample reaction vessel 100 more stably. Preferably, there are two limiting projections 154, which are respectively arranged on left and right side faces of the push rod 152. Preferably, the limiting projections 154 are arranged on the upper parts of the side faces of the push rod 152. When the push rod 152 is installed in the biological sample reaction vessel 100, the limiting projections 154 on the push rod 152, squeezed by the biological sample reaction vessel 100, causes the push rod 152 to generate elastic deformation, therefore the friction force between the push rod 152 and the biological sample reaction vessel 100 is increased, so that the push rod 152 can be installed in the biological sample reaction vessel 100 stably, and the resistance during movement of the push rod 152 is also increased.

Preferably, as shown in FIG. 14, at least one hollowed-out slot 156 is arranged at a position of the push rod 152 close to an edge, the limiting projection 154 is arranged on the outer side wall of the slot 156, and the limiting projection 154 and the slot 156 are arranged in pairs. In a specific embodiment, there are two limiting projections 154, the two limiting projections 154 are respectively arranged on the left and right side faces of the push rod 152, correspondingly, there are also two hollowed-out slots 156, which are respectively arranged at positions on the left side and the right side of the push rod close to edges, namely the outer side of the left side slot 156 is the left side face of the push rod 152, the outer side wall of the right side slot 156 is the right side face of the push rod 152, that is to say, the limiting projections 154 are arranged on the outer side walls of the slots 156. Due to the arrangement of the hollowed-out slots 156, the push rod 152 is more liable to generate deformation during action, thereby avoiding inflexible slide of the push rod 152 due to overlarge friction force.

Figure 15:
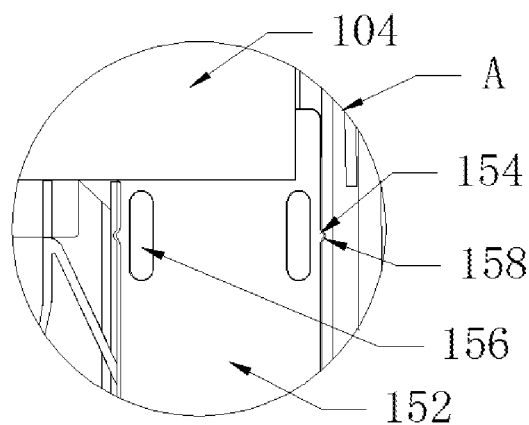
FIG. 15 is an enlarged structural diagram at A in FIG. 6.

If the push rod 152 is in a deformation state for a long time, the push rod is liable to lose certain elasticity, and thus the fastening effect is poor. In order to solve the above problem, preferably, as shown in FIG. 15, a limiting groove 158 cooperating with the limiting projection 154 is formed in the biological sample reaction vessel 100. Preferably, the limiting groove 158 for clamping the limiting projection 154 is formed in the chute 38, and the number of the limiting groove 158 is the same as that of the limiting projection 154. When the push rod 152 is in an initial state, namely, a normal state, the limiting groove 158 clamps the limiting projection 154, and the push rod 152 generates no deformation at this time; and when the push rod 152 is caused to slide by an external force, the push rod 152 generates deformation at the limiting projection 154 and leaves the limiting groove 158.

Preferably, as shown in FIG. 14, a groove 162 is formed in the push rod. The groove 162 is formed in the upper end of the push rod 152, the groove 162 is an adhesion groove for adhering the sealing element 104. Before the sealing element is adhered, the plane where the bottom of the groove 162 is located is slightly lower than the plane where the notch of the groove 162 is located, and after the sealing element 104 is adhered, the sealing element 104 fills the groove 162, so that the push rod has a flat surface. The probability that the sealing element 104 is stripped off due to being higher than the surface of the push rod 152 when the push rod 152 is pushed is avoided.

Preferably, the force-bearing portion of the push rod 152 is the bottom surface or the back of the push rod 152, when the force-bearing portion is the bottom of the push rod, the external force acts on the bottom surface of the push rod, so that the push rod 152 tears off the sealing element 104 from bottom to top, and when the force-bearing portion is the back of the push rod, the external force acts on the back of the push rod and also causes the push rod 152 to tear off the sealing element 104 from bottom to top. The force-bearing portion of the push rod 152 can also be an upper bottom surface, the left side face or the right side face of the push rod, when the force-bearing portion of the push rod is the upper bottom surface, the push rod can be pulled from above; when the force-bearing portion of the push rod is the left side face, the push rod can be pushed from left to right; and when the force-bearing portion of the push rod is the right side face, the push rod can be pushed from right to left.

In another embodiment, the force-bearing portion of the push rod 152 is in magnetic connection with an external thrust part, namely, the force-bearing portion of the push rod 152 and the external thrust part are magnetic components that attract each other, such as iron blocks, magnets or the like. The push rod 152 and the external thrust part are isolated by the biological sample reaction vessel 100, and the external thrust part drives the push rod 152 to operate under magnetic action.

Preferably, an opening is formed in the biological sample reaction vessel 100, the force-bearing portion is exposed in the opening, and the force-bearing portion receives external thrust through the opening. Namely, the external thrust part can project into the opening, come into contact with the push rod 152 in the biological sample reaction vessel 100 and cause the push rod 152 to operate, and the setting of the position of the opening is associated with the setting of the force-bearing portion of the push rod 152.

Figure 16:
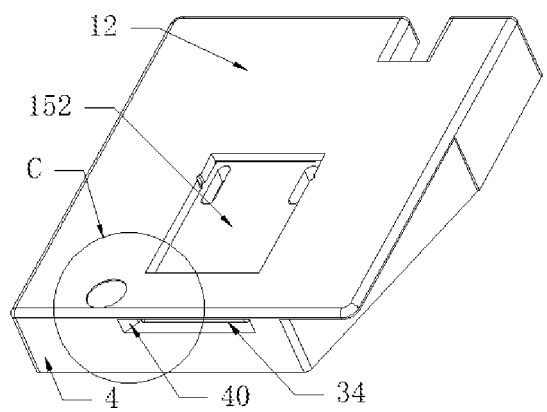
FIG. 16 is an axonometric structural diagram of connection of the box body and the push rod in the biological sample reaction vessel.
Figure 16A:
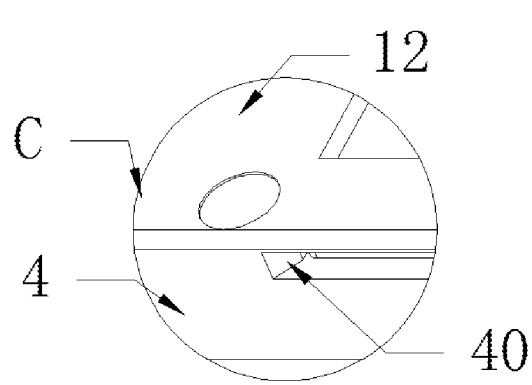
FIG. 16A is an enlarged structural diagram at C in FIG. 16.

In an embodiment, as shown in FIG. 16, the force-bearing portion of the push rod 152 is the bottom surface of the push rod, the foregoing opening 34 is formed in the bottom plate 4 of the biological sample reaction vessel 100. Preferably, as shown in FIG. 16A, a chamfer 40 is arranged on the opening 34, and the push rod 152 is completely contained in the chute 38 and at a distance from the opening 34 so as to avoid collision during misoperation. The external thrust part is introduced from the chamfer 40 of the opening 34 and projects into the chute 38 to contact the push rod 152 and bring the push rod 152 and the external thrust part into slide fit with the chute 38.

Figure 17:
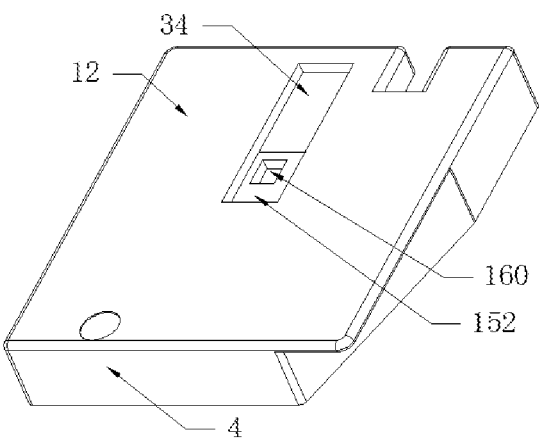
FIG. 17 is an axonometric structural diagram of another embodiment of the connection of the box body and the push rod in the biological sample reaction vessel.

In another embodiment, as shown in FIG. 17, the force-bearing portion of the push rod 152 is the back of the push rod 152, and the foregoing opening 34 is formed in the backboard 12 of the biological sample reaction vessel 100. Preferably, a convex edge or a recess 160 is arranged on the back of the push rod 152, the convex edge or the recess 160 is the force-bearing portion, and the convex edge or the recess 160 is exposed in the opening 34. The external thrust part comes into contact with the convex edge or the recess 160 and brings the push rod 152 into slide fit with the chute 38.

The reaction portion includes at least one reaction area, and the reaction area receives a reagent released by the reagent storage portion 102. The reaction portion includes a plurality of reaction areas, the setting of the number and positions of the reaction areas is related to the number of the reagent containing cavities in the reagent storage portion 102 and the reaction steps, for example, two reagents released at the same time can be temporarily stored in one reaction area and can also be temporarily stored in two independent reaction areas respectively; if a drying reagent is further deployed in the reaction area, other reaction area can also be arranged separately, the reaction areas are communicated with each other, and the reagents in the reaction areas can be mixed by rotating the biological sample reaction vessel.

As shown in FIGS. 5 and 6, a test area 28 is arranged in the reaction portion, the test area 28 can be arranged on a flow passage of any reagent of the biological sample reaction vessel 100, and the test area 28 is generally made of a transparent material, so that transmission light or scattered light emitted by an optical device can enter the biological sample reaction vessel 100. A flow guide element is arranged between the reagent storage portion 102 and the reaction portion, more specifically, the flow guide element is arranged between the reagent containing cavity and the corresponding reaction area, and the flow guide element enables the reagent in the reagent containing cavity to be released into the reaction area quickly and accurately.

Preferably, as shown in FIGS. 5 and 18, the reaction portion includes at least one reaction area, wherein at least one reaction area is a first reaction area 26, the first reaction area 26 is used for temporarily storing a solid particle reagent, the first reaction area 26 includes a supporting portion and a blocking portion, a gap 47 is formed between the supporting portion and the blocking portion, and the maximum width of the gap 47 is smaller than the minimum width of the solid particle reagent. The gap between the supporting portion and the blocking portion is used for preventing the solid particle reagent in the first reaction area from entering other reaction area(s), so that the solid particle reagent can be temporarily stored on the supporting portion stably. In an embodiment, the supporting portion is a step 46, and the blocking portion is a baffle, marked as a first baffle 48. The first baffle 48 is a vertical baffle, and the gap 47 is formed between the bottom of the first baffle 48 and the supporting portion. Preferably, the solid particle reagent is a latex freeze-dried pellet reagent. The minimum width of the latex freeze-dried pellet reagent, namely the diameter of the latex freeze-dried pellet is larger than the maximum width of the gap 47, so that the latex freeze-dried pellet reagent is blocked by the gap 47.

Preferably, as shown in FIGS. 5 and 18, the first reaction area 26 further includes a second baffle 50, the second baffle 50 is obliquely arranged, the second baffle 50 and the blocking portion from a second gap 49, the minimum width of the second gap 49 is larger than the maximum width of the solid particle reagent. The second baffle 50 and the blocking portion are used for directing the flow of the solid particle reagent, so that the solid particle reagent can smoothly enter the first reaction area 26. In a specific embodiment, the maximum width of the latex freeze-dried pellet reagent, namely the diameter of the latex freeze-dried pellet is smaller than the minimum width of the second gap 49, so that the latex freeze-dried pellet reagent can conveniently enter the first reaction area 26.

Preferably, the first baffle 48 and the second baffle 50 are baffles with radians. On the one hand, the solid particle reagent can enter quickly, and difference of diameters of solid particles is considered to avoid that the solid particles are clamped between the first baffle 48 and the second baffle 50 and cannot drop onto the step 46.

Preferably, the reaction portion further includes a second reaction area, and the second reaction area is used for temporarily storing a liquid reagent. Preferably, a flow guide element is arranged on the second reaction area, and the flow guide element includes a first flow directing plate and a second flow directing plate.

In a specific embodiment, as shown in FIGS. 5 and 6, the reaction portion includes a first reaction area 26 and a second reaction area 25, the first reaction area 26 is used for receiving the solid particles released by the reagent containing cavity 106, and the second reaction area 25 is used for receiving the liquid reagent released by the reagent containing cavity 108. A flow guide element is arranged on the second reaction area 25, and the flow guide element includes a first flow directing plate 42 and a second flow directing plate 44, so that the liquid reagent quickly flows into the second reaction area 25. The first reaction area 26 includes the step 46 for temporarily storing the reagent, the first baffle 48 and the second baffle 50, the first baffle 48 and the second baffle 50 are used for guiding the solid particles into the step 46, furthermore the gap 47 is formed between the first baffle 48 and the step 46, and the gap 47 can prevent the solid particles from entering the second reaction area 25 and allow the liquid reagent to flow into the first reaction area 26.

As shown in FIGS. 19 and 19A, the biological sample reaction vessel 100 includes a top plate 2, the bottom plate 4, a left side plate 6, a right side plate 8, a panel 10 and the backboard 12. The biological sample reaction vessel 100 is approximately a square box body and is made of a plastic material.

Preferably, as shown in FIG. 19, one end of the left side plate 6 or the right side plate 8 of the biological sample reaction vessel 100 is an inclined plane 22. Preferably, an extension portion 24 is arranged on the backboard 12 of the biological sample reaction vessel 100, and the extension portion 24 extends to the outside of the inclined plane 22. Preferably, the inclined plane 22 is arranged at a lower left corner of the biological sample reaction vessel 100. In an embodiment, the backboard 12 is square, the panel 10 is pentagonal, the left side plate 6 comprises a side face and an inclined plane, the extension portion 24 is a right triangle, and the hypotenuse of the right triangle is the connection between the backboard 12 and the extension portion 24. Due to the arrangement of the inclined plane 22 and the extension portion 24, it is convenient to manually distinguish the front and back surfaces of the biological sample reaction vessel 100, thereby avoiding inverted insertion of the biological sample reaction vessel 100 into the test cassette 200, and on the other hand, when the biological sample reaction vessel cooperates with the test cassette, the front and back surfaces of the biological sample reaction vessel can be automatically identified to avoid misoperation.

Preferably, as shown in FIG. 20, the biological sample reaction vessel 100 comprises a locating projection 16. The locating projection 16 is arranged on the panel 10, the locating projection 16 is an inverted triangle, as shown in FIG. 20A, the locating projection 16 is used for firmly locating the biological sample reaction vessel 100 in a corresponding groove of the test cassette 200, and the locating projection 16 is clamped by the groove, so that the biological sample reaction vessel 100 is fastened in the test cassette 200, thereby avoiding the displacement of the biological sample reaction vessel 100 relative to the test cassette 200 during rotation.

Preferably, as shown in FIG. 19A, a handle 14 is arranged on the top plate 2 of the biological sample reaction vessel 100, during testing, it is convenient for the user to quickly insert the biological sample reaction vessel 100 into the test cassette 200 by holding the handle 14, and after the test is completed, the biological sample reaction vessel 100 is quickly pulled out. Preferably, a notch 52 is formed in the backboard 12 of the biological sample reaction vessel 100, and due to the arrangement of the notch 52, the injection molding of the biological sample reaction vessel 100 is more convenient.

Figure 22:
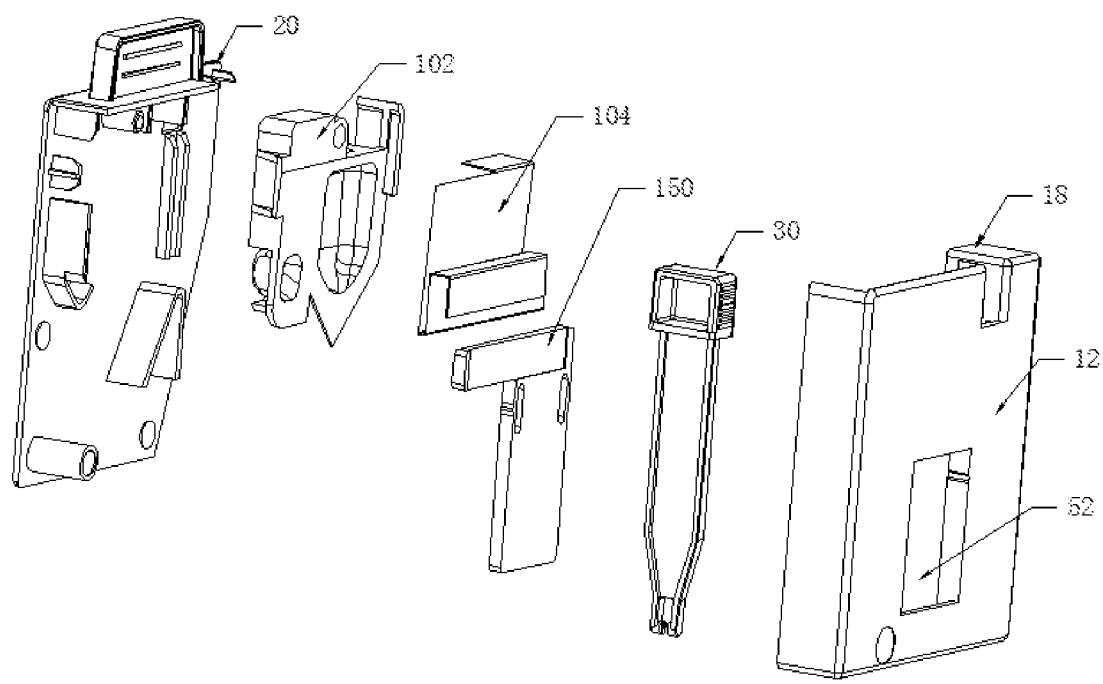
FIG. 22 is an exploded view of the biological sample reaction vessel.

In a specific embodiment, as shown in FIGS. 5, 6 and 22, the reagent storage portion 102, the reagent release portion 150, the reaction portion, the test area 28, a sampling bar 30 and a liquid absorption pad 32 are arranged in the biological sample reaction vessel 100, and the biological sample reaction vessel 100, the reagent storage portion 102, the reagent release portion 104 and the sampling bar 30 are made of a plastic material. The sampling bar 30 is used for collecting a liquid sample, such as blood, urine or the like, and adding the liquid sample to the biological sample reaction vessel 100. After the test is completed, the liquid absorption pad 32 is used for recycling waste liquid so as to avoid leakage of the liquid to cause pollution.

As shown in FIGS. 5, 6 and 22, the biological sample reaction vessel 100 is a hollow cavity and can be divided into a box body 18 and an upper cover 20, the box body 18 includes the backboard 12, the bottom plate 4, the left side plate 6 and the right side plate 8, the upper cover 20 includes the top plate 2 and the panel 10, and the upper cover 20 and the box body 18 are hermetically connected by welding or in other manner, thereby facilitating the assembly of the biological sample reaction vessel 100. The liquid absorption pad 32 is arranged above the inclined plane 22, the sampling bar 30 and the reagent storage portion 102 are arranged, next to the liquid absorption pad 32, successively in the direction toward the right side plate 8, the reaction portion and the reagent release portion 104 are both arranged below the reagent storage portion 102, and the test area 28 is arranged in the reaction portion. The sampling bar 30 is arranged in the biological sample reaction vessel 100 through an opening, and the sampling bar 30 is in clearance fit with the opening, thereby avoiding the entry of foreign matters during sampling. The inclined plane 22 is arranged on the left side of the sampling bar 30, which is beneficial for sufficient contact between the sample on the sampling bar 30 and the reaction liquid, and avoids that the sample cannot be contacted due to too little reaction liquid. The layout of the liquid absorption pad 32, the reagent storage portion 102, the sampling bar 30, the reaction portion and the reagent release portion 104 is not limited to that described above. Preferably, the second flow directing plate 44 is connected with the upper end of the first baffle 48, the upper end of the first flow directing plate 42 is further connected with a sampling needle guide plate 57, and the sampling needle guide plate 57 is arranged in a vertical direction. As shown in FIGS. 12 and 20B, the box body 18 and the upper cover 20 both comprise sampling needle fixing parts 59, and the sampling needle fixing parts 59 are used for avoiding shaking of the box body and the upper cover.

Figure 21:
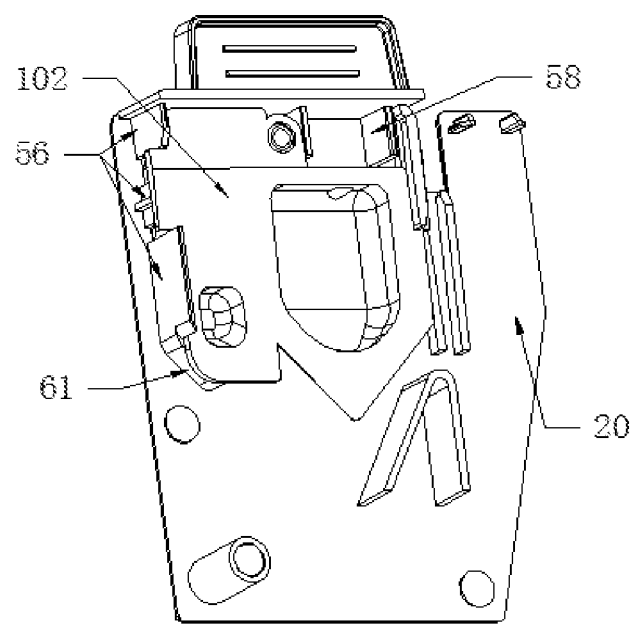
FIG. 21 is a schematic diagram of a connecting structure of the upper cover and the reagent storage portion in the biological sample reaction vessel.

In a specific embodiment, the reagent storage portion and the biological sample reaction vessel are connected in such a manner as shown in FIG. 8A, wherein locating elements are arranged on the reagent storage portion 102, the locating elements constitute a cavity for containing the reagent storage portion 102, so that the reagent storage portion 102 is fixedly installed in the biological sample reaction vessel 100. The cavity can also adopt conventional technical means in the prior art. In a specific embodiment, as shown in FIGS. 12, 12A, 20 and 20B, a locating column 54 and a supporting plate 61 are arranged on the panel 10, left side locating plates 56 and right side locating plates 58 are a plurality of dispersive locating elements, which are dispersively arranged on the box body 18 and the upper cover 20, and the above locating elements are used for fixedly connecting the reagent storage portion 102. As shown in FIGS. 8A and 8B, the locating elements of the reagent storage portion 102 include a mounting hole 122, a left locating element 124, a right locating element 126 and a lower locating element 128. As shown in FIG. 21, the mounting hole 122 is sleeved on the locating column 54 for fixing the upper end of the reagent storage portion 102; and the left locating element 124 and the right locating element 126 are respectively in limiting connection with the left side locating plates 56 and the right side locating plates 58, and the lower locating element 128 is placed on the supporting plate 61. Therefore, the reagent storage portion 102 is stably installed in the biological sample reaction vessel 100, and the displacement of the reagent storage portion 102 during movement or shaking of the biological sample reaction vessel 100 is avoided. The preferred embodiments and implementations mentioned above can be randomly selected and combined according to requirement to achieve the ultimate objective of fast sample concentration testing.

As shown in FIGS. 23 and 24, an ejection rod 204 is arranged in the test cassette 200, and the ejection rod 204 comes into contact with the force-bearing portion through the opening 34 in the biological sample reaction vessel and provides an acting force of the external device.

Preferably, the ejection rod 204 is movable relative to the test cassette 200. The ejection rod 204 may be fixedly installed on the box body, and may also be movable relative to the box body. If the ejection rod 204 is movable, the external device controls a movement area and a movement position of the ejection rod 204, for example, the movement of the ejection rod 204 can be controlled by a motor, and conventional technology in the prior art can also be adopted. If the ejection rod 204 is fixed to the box body, when the biological sample reaction vessel 100 is inserted into the test cassette 200 of the external device, the ejection rod 204 and the push rod 152 are brought into cooperation by means of an insertion force so as to drive the push rod 152 to operate.

Preferably, the ejection rod 204 is arranged on the bottom plate of the test cassette 200 or the ejection rod 204 is arranged on inner side panel of the test cassette 200. As shown in FIG. 25, when the test cassette 200 cooperates with the force-bearing portion which is the bottom surface of the push rod 152, the opening 34 is formed in the bottom plate 4 of the biological sample reaction vessel 100, and the ejection rod 204 is arranged on the bottom plate of the test cassette 200. Preferably, a chamfer is arranged on the upper end part of the ejection rod 204, so that the ejection rod 204 can conveniently project into the opening 34. When the test cassette 200 cooperates with the force-bearing portion which is the back of the push rod 152, the opening 34 is formed in the backboard 12 of the biological sample reaction vessel 100, and the ejection rod 204 is arranged on the inner side panel of the test cassette 200.

Preferably, as shown in FIGS. 24 and 26, a movable plate is arranged in the test cassette 200, the movable plate includes a substrate 206 and an elastic element 210, and the substrate 206 is fixedly connected to the inner wall of the test cassette 200 through the elastic element 210. Preferably, two elastic elements 210 are provided, each elastic element 210 includes an installation surface 212 and two elastic arms 214, the installation surface 212 is fixedly connected with the inner side face of the test cassette 200, and the two elastic arms 214 are fixedly connected with the substrate 206 respectively.

Preferably, the substrate 206 is a heating plate, which is marked as a first heating plate. That is, the movable plate serves as both a heating element and an elastic fastener.

Preferably, as shown in FIGS. 23 to 27, an elastic sheet 216 is arranged on one inner side face of the test cassette 200. Preferably, the elastic sheet 216 is arranged on one inner side face adjacent to the movable plate. The elastic sheet 216 comprises an elastic arm 218, one end of the elastic arm 218 is fixed to the elastic sheet 216, the other end of the elastic arm 218 is in the shape of a smooth curved surface, and the elastic arm 218 is installed facing to the inner hollow cavity of the test cassette 200. The elastic sheet 216 is used for cooperating with the inclined plane 22 on the biological sample reaction vessel 100, therefore one side of the biological sample reaction vessel 100 provided with no inclined plane is tightly fit to the inner side wall of the test cassette 200. As the elastic sheet 216 has certain elasticity, in the case of inverted insertion of the biological sample reaction vessel 100 into the test cassette 200, the biological sample reaction vessel 100 cannot be completely fit into the test cassette 200 due to the effect of the elastic sheet 216, therefore correct insertion of the biological sample reaction vessel 100 can be identified by means of the cooperation of the elastic sheet 216 and the inclined plane 22.

Preferably, as shown in FIG. 23, a groove 202 is formed in one inner side face of the test cassette 200. Preferably, the groove 202 is formed in the inner side face opposite to the movable plate. The groove 202 is used for clamping the locating projection 16 on the biological sample reaction vessel 100, so that the biological sample reaction vessel 100 can be clamped on the groove 202, thereby avoiding the displacement of the biological sample reaction vessel 100 during rotation or shaking of the test cassette 200.

In a specific embodiment, as shown in FIGS. 4, 23 and 24, the test cassette 200 is fixed to the external device to achieve uniform mixing or rotation, the test cassette 200 includes a box body with an open end, an optical aperture 201 is formed in the box body, the ejection rod 204, a first heating plate 206 and a second heating plate 208 are arranged in the box body, the first heating plate 206 is the movable plate, the ejection rod 204 comes into contact with the force-bearing portion through the opening 34 and provides external thrust, and the first heating plate 206 and the second heating plate 208 are used for heating the reagent so as to satisfy the requirement of the reaction temperature.

As shown in FIG. 25, when the biological sample reaction vessel 100 is inserted into the test cassette 200, the biological sample reaction vessel 100 presses the first heating plate 206, the first heating plate 206 causes the elastic element 210 to generate deformation under the action of pressure, and then the biological sample reaction vessel 100 can be quickly inserted, and the locating projection 16 is buckled into the groove 202. Meanwhile, the inclined plane 22 of the biological sample reaction vessel 100 compresses the elastic sheet 216, so that the test area 28 on the biological sample reaction vessel 100 is aligned with the optical aperture 201 in the test cassette 200. During insertion of the biological sample reaction vessel 100 into the test cassette 200, the ejection rod 204 projects into the opening 34 to contact the push rod 152, when the biological sample reaction vessel 100 moves from top to bottom, the push rod 152 moves from bottom to top to drive the sealing element 104 to move from bottom to top, so that the sealing element 104 is torn off from the reagent storage portion 102 to release the reagent, as shown in FIG. 7A.

At present, there are many methods for testing glycosylated hemoglobin available in the market, wherein the commonly used test methods include ion exchange chromatography, affinity chromatography, high pressure liquid phase, immunization, ion capture and electrophoresis methods and the like. The immunization method means that after erythrocytes are dissolved, HbA1c is measured based on the interaction of antigen molecules and special antibodies.

The test of HbA1c by the immunoagglutination method includes the following two test steps: respectively testing the concentration of total hemoglobin Hb and the concentration of glycated hemoglobin HbA1c in a sample. The test of the total hemoglobin (Hb) includes: oxidizing ferrous ions in the hemoglobin by using potassium ferricyanide to generate methemoglobin, carrying out the reaction of the methemoglobin with thiocyanate to generate thiocyanic acid methemoglobin, and testing the light absorption value at 531 nm to obtain the concentration of Hb. The test of the glycated hemoglobin (HbA1c) includes: a lectin containing a plurality of HbA1c immunoreaction binding sites competes with HbA1c in the blood to combine with an anti-HbA1c antibody marked on a latex microsphere, wherein the combination of the former will lead to a change of the turbidity of the reaction liquid, and the concentration of the HbA1c in the blood can be obtained by testing the light absorption value at 531 nm. The higher the concentration of the HbA1c in the blood, the lower the turbidity is, the smaller the light absorption value is, and the variations of the light absorption value and the concentration of the HbA1c are obtained by a calibration curve.

Figure 28:
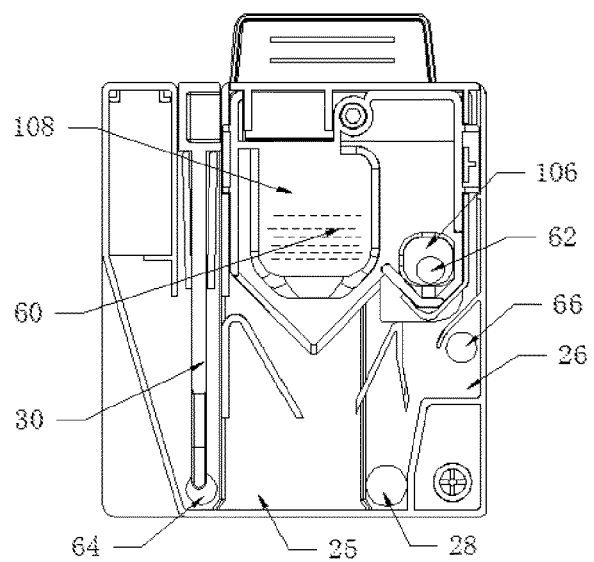
FIG. 28 is a schematic diagram of a reagent state at step 0 during testing with the biological sample reaction vessel.

Therefore, in the test of the HbA1c by using the immunization method, a thiocyanate liquid reagent (Buffer), a latex pellet marked with the anti-HbA1c antibody, a potassium ferricyanide drying reagent (drying object) and a lectin drying reagent (drying object) containing a plurality of HbA1c immunoreaction binding sites need to be used. As shown in FIG. 28, the thiocyanate liquid reagent 60 is stored in the reagent containing cavity 108, the latex pellet 62 marked with the anti-HbA1c antibody is stored in the reagent containing cavity 106, the potassium ferricyanide drying reagent 64 is cured on the second reaction area 25, and the lectin drying reagent 66 is cured in the first reaction area 26.

Figure 28A:
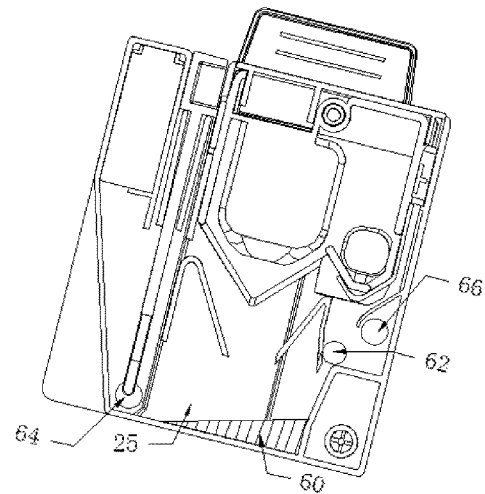
FIG. 28A to FIG. 28F are respectively schematic diagrams of reagent states at steps 1-6 during testing with the biological sample reaction vessel.
Figure 28B:
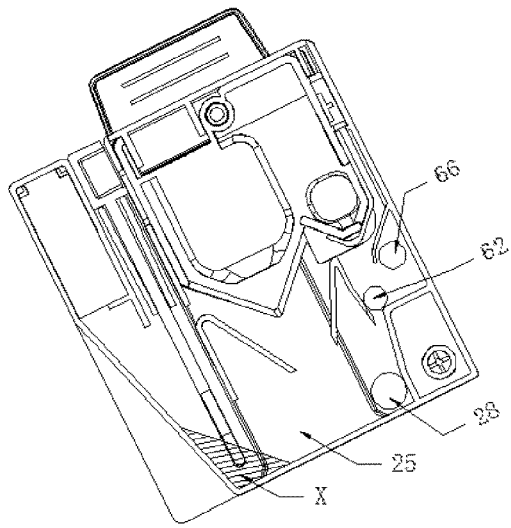
Figure 28C:
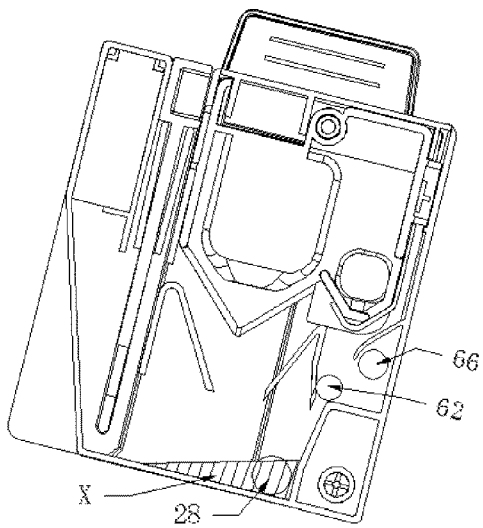
Figure 28D:
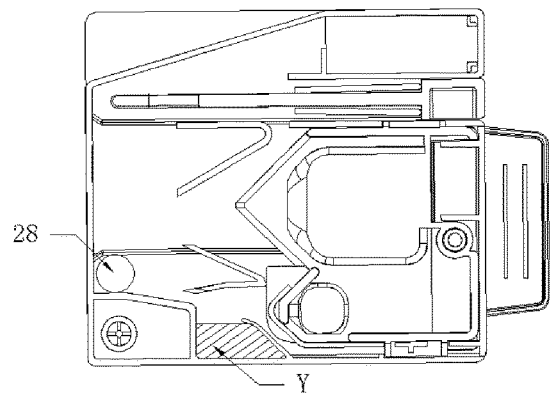
Figure 28E:
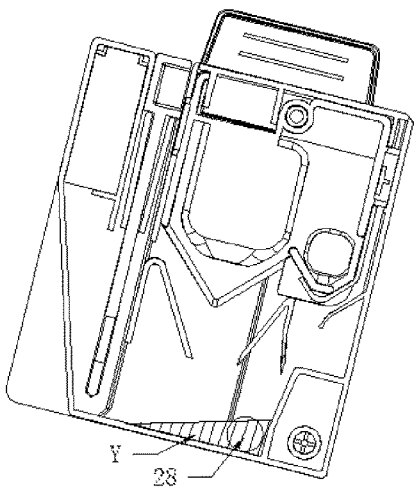
Figure 28F:
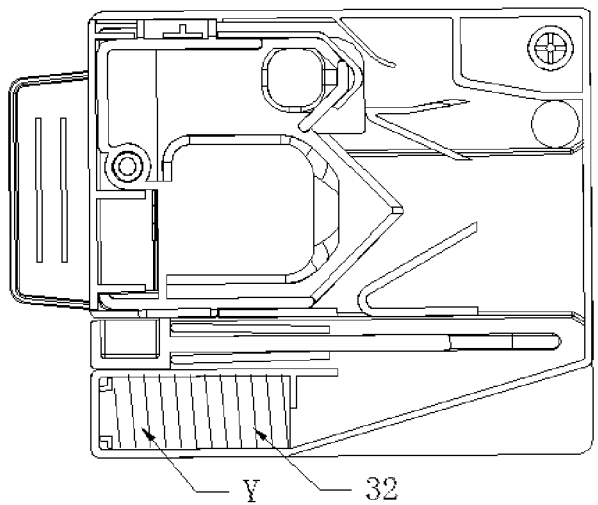
Figure 29:
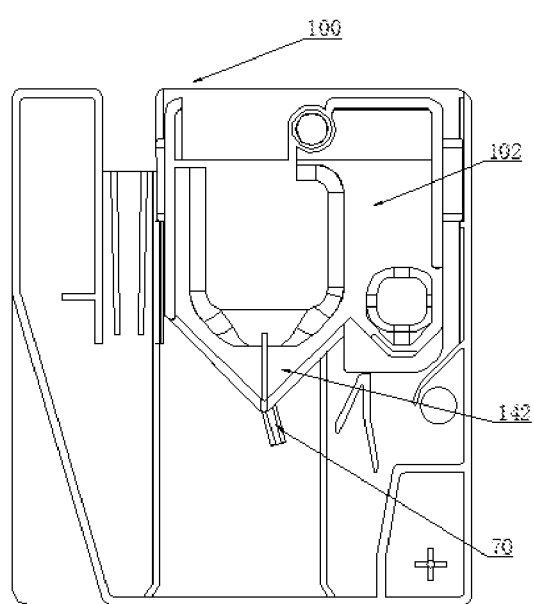
FIG. 29 is a structural schematic diagram of a flow guide rib on the reaction vessel.
Figure 30:
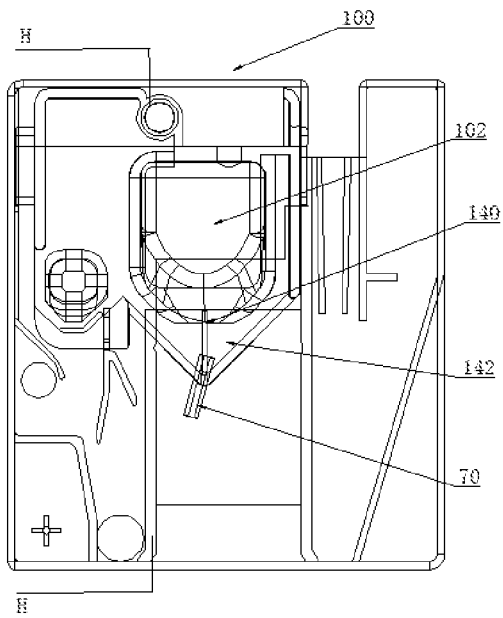

The latex pellet is a small latex freeze-dried pellet, a specific HbA1c antibody is connected to the small latex pellet through a covalent binding method in advance, and the latex pellet is quickly frozen to the small pellet having the same volume by using the freeze drying technology, thereby maximally protecting the reactivity of the latex antibody and greatly prolonging the useful life and storage life at normal temperature. The concentration of the HbA1c in the blood is tested by using the biological sample reaction vessel of the present invention. The steps of testing the HbA1c through the immunization method are as follows:

Step 0: as shown in FIG. 28, inserting the sampling bar 30 with a sample into the biological sample reaction vessel;

step 1: as shown in FIG. 28A, rotating the test cassette, inserting the biological sample reaction vessel into the test cassette, tearing off the sealing element 104 by the upward movement of the push rod 152 under the action of the external thrust, and releasing the latex pellet 62 and the thiocyanate 60 at the same time, wherein the latex pellet 62 drops into the first reaction area 26 for temporary storage, and the thiocyanate liquid reagent 60 drops into the test area 28 of the second reaction area 25;

step 2: as shown in FIG. 28B, rotating the biological sample reaction vessel to mix the Buffer 60 (thiocyanate), the drying object 64 (potassium ferricyanide) and the blood sample to form a mixture X;

step 3: as shown in FIG. 28C, rotating the biological sample reaction vessel to rotate the mixture X in the step 2 to the test area 28, and testing the content of the hemoglobin (Hb) in the sample;

step 4: as shown in FIG. 28D, continuing to rotate the biological sample reaction vessel, so that the mixture X in the step 2 enters the first reaction area 26, and the mixing the mixture with the drying object 66 (lectin containing a plurality of HbA1c immunoreactions binding sites) and the latex pellet 62 (latex pellet marked with the anti-HbA1c antibody) to form a mixture Y;

step 5: as shown in FIG. 28E, rotating the biological sample reaction vessel to cause the mixture Y in the step 4 to enter the reaction area 28, and testing the content of the glycosylated hemoglobin (HbA1C) in the sample; and step 6: as shown in FIG. 28F, rotating the biological sample reaction vessel to cause make the mixture Y in the step 4 to enter the liquid absorption pad 32, so that the waste liquid after the reaction is absorbed.

After the test of the HbA1c is ended, the external device calculates and outputs a test structure.

The biological sample reaction vessel of the present invention is not limited to the test of the HbA1c in the above blood sample, can also be applied to the test of other biological samples, such as urine, saliva, spinal fluid and the like, and can also be applied to the test of the concentration of C-reactive protein, cholesterol, blood fat, blood glucose and other analytes.

In the above description, conventional technological means in the prior art is employed unless otherwise specified.

What is claimed is:

1. A biological sample reaction vessel, comprising:
a reagent storage portion, a reaction portion, and a push rod packaged in the sample reaction vessel;
wherein the reagent storage portion comprises at least one reagent containing cavity, and the reagent containing cavity is sealed within the sample reaction vessel by a sealing element affixed to a surface of the reagent storage portion and overlying the reagent containing cavity; and
wherein the sample reaction vessel is configured and arranged such that the push rod is configured and arranged to be movable relative to the reagent storage portion from a first position to a second position due to a force applied to the push rod by an external device which receives the sample reaction vessel, and wherein the push rod is operably connected to the sealing element such that the movement of the push rod to the second position releases reagent from the reagent storage portion into the reaction portion by separating the sealing element from the surface of the reagent storage portion, thereby uncovering the reagent containing cavity.

2. The biological sample reaction vessel of claim 1, wherein the push rod is defined as having a top surface attached to the sealing element, a bottom surface distal from the top surface, a front surface facing the reagent storage portion, and a rear surface distal to the front surface and is configured and arranged such that when the external device applies the force to the rear surface or bottom surface of the push rod, the force causes the push rod to move from the first position to the second position.

3. The biological sample reaction vessel of claim 2, wherein the force is applied to the rear surface of the push rod.

4. The biological sample reaction vessel of claim 2, wherein the force is applied to the bottom surface of the push rod.

5. The biological sample reaction vessel of claim 1, wherein a chute is formed in the reaction vessel, wherein the chute is configured and arranged such that the push rod is inserted into the chute.

6. The biological sample reaction vessel of claim 5, wherein an isolating plate is arranged on the chute, wherein the isolating plate is configured and arranged to prevent reagents within the reaction vessel from entering the chute.

7. The biological sample reaction vessel of claim 1, wherein at least one projection is arranged on at least one surface of the push rod.

8. The biological sample reaction vessel of claim 1, wherein the push rod is configured and arranged such that a portion of the sealing element remains affixed to the surface of the reagent storage portion when the push rod moves from the first position to the second position.

* * * * *